(12) United States Patent
Nam et al.

(10) Patent No.: US 7,728,193 B2
(45) Date of Patent: Jun. 1, 2010

(54) PHYTOCHROME-INTERACTING PROTEIN AND A USE THEREOF

(75) Inventors: Hong-Gil Nam, Pohang (KR);
Jong-Sang Ryu, Seong-nam (KR);
Pyung-Ok Lim, Pohang (KR);
Ja-Choon Koo, Gangseo-gu (KR)

(73) Assignees: Genomine Inc., Pohang, Kyungsangbuk-Do (KR); Postech Foundation, Pohang, Kyungsangbuk-Do (KR)

( * ) Notice: Subject to any disclaimer, the term of this patent is extended or adjusted under 35 U.S.C. 154(b) by 657 days.

(21) Appl. No.: 10/590,551

(22) PCT Filed: Feb. 28, 2005

(86) PCT No.: PCT/KR2005/000557

§ 371 (c)(1),
(2), (4) Date: Aug. 24, 2006

(87) PCT Pub. No.: WO2005/082931

PCT Pub. Date: Sep. 9, 2005

(65) Prior Publication Data

US 2008/0235826 A1 Sep. 25, 2008

(30) Foreign Application Priority Data

Feb. 27, 2004 (KR) ............... 10-2004-0013663

(51) Int. Cl.
*C12N 15/82* (2006.01)
*A01H 5/00* (2006.01)
*A01H 5/10* (2006.01)

(52) U.S. Cl. .............. 800/298; 800/278; 800/290; 800/320

(58) Field of Classification Search ............ None
See application file for complete search history.

(56) References Cited

U.S. PATENT DOCUMENTS 6,660,511 B1 * 12/2003 Luo et al. ............. 435/196

OTHER PUBLICATIONS

NCBI Accession No. AAQ22649 dated Aug. 12, 2003.
Fankhauser et al., "Light receptor kinases in plants," *Current Biology*, 1999, vol. 9, pp. R123-R126, Elsevier Science, Oxford, England.
Neff et al., "Light: an indicator of time and place," *Genes & Development*, 2000, vol. 14, pp. 257-271, Cold Spring Harbor Laboratory Press, Cold Spring Harbor, New York.
Das et al., "The structure of the tetratricopeptide repeats of protein phosphatase 5: implications for TPR-mediated protein-protein interactions," *The EMBO Journal*, 1998, vol. 17, No. 5, pp. 1192-1199, Oxford University Press, Oxford, England.

* cited by examiner

*Primary Examiner*—Stuart F. Baum
(74) *Attorney, Agent, or Firm*—Buchanan Ingersoll & Rooney PC

(57) ABSTRACT

The present invention relates to a novel protein interacting with phytochromes and use thereof, and more particularly, to a polypeptide having either an amino acid sequence set forth in SEQ ID NO: 4 or an amino acid sequence having at least 70% with said amino acid sequence, and use thereof. The polypeptide interacts with phytochromes A and B, and the TPR domain present at the N-terminal region of the polypeptide is involved in the interaction. Also, a PP2A catalytic domain (PP2Ac) having phosphatase activity is present at the C-terminal region of the polypeptide. The polypeptide can be used as a phosphatase, and is useful in the production of plants sensitive to light signal transduction. Furthermore, the TPR domain present in the polypeptide is useful in the production of dwarf plants.

5 Claims, 12 Drawing Sheets phyA

Bait Fusion-
protein

PHYTOCHROME-INTERACTING PROTEIN AND A USE THEREOF

TECHNICAL FIELD

The present invention relates to a novel protein involved in phytochrome light signal transduction mechanisms and a use thereof, and more particularly, to a type 5 serine/threonine phosphatase interacting with phytochromes and a use thereof.

BACKGROUND ART

To perceive the status of their light environment, plants have evolved various photoreceptors. The photoreceptors (an unidentified UV-B receptor, a phototropin and cryptochrome sensing TV-A/blue light region of the spectrum, and phytochromes sensing red (R)/far-red (FR) region of the spectrum) mediate signals to genes regulating the growth and development of plants (Fankhauser, C. & Chory, J. *Curr. Biol.*, 9:R123-R126, 1999; Neff, M. M., et al., *Genes Dev.*, 14:257-271, 2000). The recent development of molecular biological and biochemical research technologies and molecular genetic research technologies have been made in the molecular cloning and genetic characterization of the photoreceptors themselves, as well as some signal intermediate components involved in transducing perceived signals from photoreceptors to photoresponsive genes (Quail, P. H. *Curr. Opin. Cell. Biol.*, 14:180-188, 2002; Gyula, P. et al., *Curr. Opin. Plant Biol.*, 6:446-452, 2003).

Phytochromes are photoreceptors whose characteristics were most well studied, that regulate various aspects of the growth and development of higher plants. Depending to the spectrum of light irradiated on phytochromes, a reversible photo-conversion occurs between a biologically inactive, red light-absorbing form (Pr) and a biologically active, far-red light-absorbing form (Pfr). The photo-conversion into the Pfr form by red light treatment initiates translocation from the cytoplasm of phytochromes themselves to the nucleus, and activates the signal transduction pathway inducing various effects on the expression and development of genes, thus regulating the growth and development of plants (Quail, P. H. *Curr. Opin. Cell. Biol.*, 14:180-188, 2002; Fankhauser, C. & Chory, J. *Curr. Biol.*, 9:R123-R126, 1999). It is reported that there are five different phytochromes (designated phyA, phyB, phyC, phyD and phyE) in *Arabidopsis thaliana* (Neff, M. M., et al., *Genes Dev.*, 14:257-271, 2000; Quail, P. H. *Curr. Opin. Cell. Biol.*, 14:180-188, 2002).

The generic phytochromes consist of an apoprotein of about 116-121 kDa and a tetrapyrrole chromophore, phytochromobillin that is covalently linked to the apoprotein (Quail, P. H. *Curr. Opin. Cell. Biol.* 14:180-188, 2002; Gyula, P. et al., *Curr. Opin. Plant Biol.*, 6:446-452, 2003). The photosensoty activity of phytochromes resides in their unique capacity for reversible, light-induced interconversion between the Pr form and the Pfr form. The monomer of phytochrome molecule is composed of a globular N-terminal domain (~70 kDa), which is anchoring the chromophore, and a C-terminal domain linked via a flexible hinge region. The N-terminal domain is responsible for photosensory function. Also, the conformationally open C-terminal domain (about 55 kDa) is known to be involved in signal transfer (Quail, P. H. *Curr. Opin. Cell. Biol.*, 14:180-188, 2002; Gyula, P. et al., *Curr. Opin. Plant Biol.*, 6:446-452, 2003). The C-terminal domain contains a pair of the Per-Arnt-Sim (PAS) motifs around the regulatory core region. The PAS motifs are known to be involved in protein-protein interaction and inter-domain communications in some sensory proteins. The results of analysis with recombinant oat phytochrome A showed that the C-terminal domain of phytochromes possesses serine/threonine protein kinase activity (Yeh, K. C. & Lagarias, J. C. *Proc. Natl. Acad. Sci. U.S.A.* 95:13976-13981, 1998; Fankhauser, C. et al., *Science*, 284:1539-1541, 1999). Furthermore, it was suggested by the results of spectral and photochemical tests that the photo-isomerization of phytochromes induced by chromopores triggers conformational changes throughout the whole phytochrome molecule via inter-domain communication within the molecules, like the well-characterized rhodopsin visual receptor in animals (Maeda, T. et al., *Prog. Retin. Eye Res.*, 22:417-434, 2003; Vishnivetskiy, S. A. et al., *J. Biol. Chem.*, 275:41049-41057, 2000). In addition, the conformational signals of phytochrome could be further differentiated by inter-domain interactions in the phytochrome molecule, and this is presumed to be modulated by reversible phosphorylation/dephosphorylation at serine residue in the hinge region. In spite of these many authentic findings, however, minute mechanisms by which the phytochromes transduce light signals to photoresponsive genes are not yet completely established.

DISCLOSURE OF THE INVENTION

Therefore, during extensive studies to establish the light signal transduction mechanism of phytochromes and to identify new mediator molecules involved therein, the present inventors have found a novel protein interacting with phytochromes and identified the functions and characteristics thereof, thus completing the present invention. Accordingly, an object of the present invention is to provide a novel protein interacting with phytochromes and use thereof.

To achieve the above object, in one aspect, the present invention provides an isolated polypeptide having an amino acid sequence set forth in SEQ ID NO: 4 or an of SEQ ID NO: 4.

In another aspect, the present invention provides an isolated polynucleotide having a nucleotide sequence encoding said polypeptide or a nucleotide sequence complementary to said nucleotide sequence, and a recombinant vector comprising the same.

Also, the present invention provides a cell comprising said recombinant vector.

In still another aspect, the present invention provides a method for producing a plant sensitive to light signal transduction, comprising introducing said polynucleotide encoding the polypeptide into a plant.

In still another aspect, the present invention provides a method for producing a dwarf plant, comprising introducing a polynucleotide encoding the sequence of amino acids 1-138 of SEQ ID NO: 4 into a plant.

In yet another aspect, the present invention provides a method of identifying a phytochrome signal transduction-associated substance using said polypeptide or a polynucleotide encoding the polypeptide.

Also, the present invention provides a method of identifying a plant dwarfism-causing substance using a polypeptide encoding the sequence of amino acids 1-138 of SEQ ID NO: 4 or a polynucleotide encoding the polypeptide.

Furthermore, the present invention provides a method of preparing a protein having phosphatase activity using said polynucleotide encoding the polypeptide.

Hereinafter, the present invention will be described in detail.

The present invention provides novel protein PAPP5 interacting with phytochromes. The PAPP5 protein is a kind of type 5 serine/threonine protein phosphatase, and its N-terminal region has three TPR (tetratricopeptide repeats) motifs which are involved in interaction with phytochromes. The C-terminal region of the inventive PAPP5 protein exhibits phosphatase activity. This enzymatic activity is inhibited by an okadaic acid, and on the contrary, is promoted by an arachidonic acid. This enzymatic activity of the PAPP5 protein is regulated by an allosteric change caused by a TPR domain at N-terminus. Also, the PAPP5 has the activity of dephosphorylating autophosphorylated phytochromes, mainly the Pfr phytochrome.

The polypeptide according to the present invention includes a polypeptide having an amino acid sequence of SEQ ID NO: 4 and functional equivalents thereof. As used herein, the term "functional equivalents" refers to polypeptides having substantially the same physiological activity as the protein of SEQ ID NO: 4, which have a sequence homology of at least 70%, preferably at least 80%, and more preferably at least 90% with the amino acid sequence of SEQ ID NO: 4, as a result of the addition, substitution or deletion of amino acids. As used herein, "substantially the same physiological activity" means phosphatase activity. The functional equivalents include, for example, amino acid sequence variants with substitutions, deletions or substitutions in some of the amino acids of the polypeptide having the amino acid sequence of SEQ ID NO: 4. Preferably, the substitutions of amino acid is conservative substitutions. Examples of conservative substitutions of amino acid occurring in nature are as following: Aliphatic amino acids (Gly, Ala, Pro), hydrophobic amino acids (Ile, Leu, Val), aromatic amino acids (Phe, Tyr, Trp), acidic amino acid (Asp, Glu), basic amino acids (His, Lys, Arg, Gln, Asn) and sulfur-containing amino acids (Cys, Met). The deletions of amino acids are preferably located in portions which are not involved directly in the physiological activity of PAPP5. A preferred functional equivalent of the inventive polypeptide may be a polypeptide (SEQ ID NO: 14) with deletions of amino acids 1-138 in SEQ ID NO: 4. The polypeptide with the deletions has a homology of 77.8% to the PAPP5 protein. Furthermore, the scope of the functional equivalents also encompasses polypeptide derivatives having partial modifications of the chemical structure of the inventive polypeptide while maintaining the basic backbone and physiological activity of the inventive polypeptide. For example, it encompasses structural modifications for modifying the stability, storage, volatility or solubility of the inventive polypeptide.

The inventive polypeptide may be extracted from the nature (e.g., plant cells) or obtained by the expression of a recombinant nucleic acid encoding the inventive polypeptide or by chemical synthesis. Preferably, it can be isolated from *Arabidopsis thaliana*. The inventive polypeptide may be easily prepared by any chemical synthesis method known in the art (Creighton, Proteins; Structures and Molecular Principles, W.H. Freeman and Co., NY, 1983). Typical synthesis methods include, but are not limited to, liquid or solid phase synthesis, fragment condensation, F-MOC or T-BOC chemical method (Chemical Approaches to the Synthesis of Peptides and Proteins, Williams et al., Eds., CRC Press, Boca Raton Fla., 1997; A Practical Approach, Athert on & Sheppard, Eds., IRL Press, Oxford, England, 1989).

Furthermore, the inventive polypeptide may also be constructed by a genetic engineering method. For this purpose, a DNA sequence encoding a PAPP5 or fragment thereof is first constructed according to the conventional method. The DNA sequence may be constructed by performing PCR amplification with suitable primers. Moreover, the DNA sequence may also be synthesized by the standard methods known in the art, for example, using an automatic DNA synthesizer (Biosearch or Applied Biosystem). The constructed DNA sequence is operably linked to expression control sequences and inserted into a vector containing one or more expression control sequences (e.g., promoters, enhancers, etc) that control the expression of the DNA sequence. Host cells are transformed with the resulting vector. The transformed cells are cultured in suitable medium and conditions for the expression of the DNA sequence, and a substantially pure polypeptide encoded by the DNA sequence is collected from the cell culture. The collection can be performed by any method known in the art (e.g., chromatography). As used herein, "substantially pure polypeptide" means that the polypeptide according to the present invention substantially contains no other proteins derived from host cells. For further information on the genetic engineering method for the synthesis of the inventive polypeptide, see the following references: Maniatis et al., Molecular Cloning; A laboratory Manual, Cold Spring Harbor laboratory, 1982; Sambrook et al., supra; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

In another aspect, the present invention provides an isolated polynucleotide having a nucleotide sequence encoding the PAPP5 and functional equivalents thereof. The polynucleotides include DNA, cDNA and RNA sequences. Namely, the polynucleotide may have a nucleotide sequence encoding either an amino acid sequence of SEQ ID NO: 4 or an amino acid sequence having a homology of at least 70% with the amino acid sequence of SEQ ID NO: 4, or a nucleotide sequence complementary to said nucleotide sequence. The polynucleotide may preferably have a nucleotide sequence set forth in SEQ ID NO: 3 or SEQ ID NO: 15.

The inventive polynucleotide may be operably linked to expression control sequences. The term "operably linked" means that one nucleic acid fragment binds to other nucleic acid fragment so that the function or expression of one is affected by the other. Also, the term "expression control sequence" refers to a DNA sequence which controls the expression of operably linked nucleic acid sequences in certain host cells. Such expression control sequence includes a promoter for initiation of transcription, an optional operator sequence for control of transcription, a sequence encoding suitable mRNA ribosomal binding sites, and sequences which control the termination of transcription and translation.

The inventive polynucleotide may be inserted into a suitable expression vector. As used herein, the term "expression vector" refers to a plasmid, virus or other mediator known in the art, into which the inventive polynucleotide can be inserted. Vectors suitable for introducing the inventive polynucleotide into plant cells include, but are not limited to, Ti-plasmids, root-inducing (Ri)-plasmids and plant virus vectors. Preferably, a pNB96 vector may be used.

The recombinant vector comprising the inventive polynucleotide may be introduced into a cell using any method known in the art. The cell may be a eukaryotic cell, such as yeast and plant cell, or a prokaryotic cell, such as *E. coli*. Preferably, the cell may be *E. coli* cell or *Agrobacterium* sp. cells The known method which can be used to introduce the inventive vector into host cell includes, but are not limited to, *Agrobacterium*-mediated transformation, particle gun bombardment, silicon carbide whiskers, sonication, electroporation, and PEG (polyethylenglycol) precipitation. In still another aspect, the present invention provides the cell transformed with the inventive recombinant vector. The cell includes, but is not limited to, a eukaryotic cell, such as yeast and plant cell, or a prokaryotic cell, such as *E. coli*.

In still another aspect, the present invention provides a method for producing a plant sensitive to light signal transduction by overexpressing the polynucleotide encoding the polypeptide in the plant. This method comprises the steps of:

(a) inserting a polynucleotide encoding the inventive PAPP5 or a functional equivalent thereof into an expression vector; and (b) introducing the expression vector into a plant.

The polynucleotide may have a nucleotide sequence set forth in SEQ ID NO: 3 or SEQ ID NO: 15. The expression vector which can be used in the above method may be preferably a vector comprising a promoter inducing the overexpresion of gene (e.g., CaMV 35S promoter). For example, there is a pNB96 vector. As used herein, the term "overexpression" means that a gene is expressed at a higher level than that in wild-type plants. The method which can be used to introduce the inventive polynucleotide-containing expression vector into the plant is as described above. Preferably, the *Agrobacterium*-mediated transformation may be used.

In yet another aspect, the present invention provides a transgenic plant produced by the above method. The inventive polypeptide-overexpressing plant produced by the above method has a characteristic in that it is sensitive to light signal transduction. Namely, it shows strong de-etiolation (a short hypocotyl phenotype that is the phenomenon of light sensitivity) in a continuous red light-high irradiance response (Rc-HIR) and a continuous far-red light-high irradiance response (FRc-HIR), as compared to wild-type plant. Also, it strongly shows an "End-Of-Day Far-Red" (EOD-FR) response that is mediated by a phytochrome B, and anthocyanin accumulation that is a phytochrome A-mediated response, as compared to wild-type plants. Since the PAPP5-overexpressing transgenic plant is sensitive to light, it has an advantage in that its growth is not inhibited even under the condition of weak intensity light or small amount light so that the plant can be normally grown. In yet another aspect, the present invention provides a plant tissue or seed derived from the transgenic plant.

In still another aspect, the present invention provides a method for producing a dwarf plant by overexpressing a polynucleotide encoding a fragment of said polypeptide in a plant. This method comprises the steps of:

(a) introducing a polynucleotide encoding the sequence of amino acids 1-138 of SEQ ID NO: 4 into an expression vector; and (b) introducing the expression vector into a plant.

The polynucleotide encodes the TPR domain of the inventive polypeptide PAPP5. Preferably, the polynucleotide has a nucleotide sequence encoding the sequence of amino acids 1-138 of SEQ ID NO: 4. The expression vector into which the polynucleotide is introduced, and the method for introducing the expression vector into the plant, are as described above for the production method of the light-sensitive plant. Preferably, the pNB96 vector and the *Agrobacterium*-mediated transformation may be used. Furthermore, the present invention provides a transgenic plant produced by said method and a plant tissue and seed derived the transgenic plant. The TPR domain-overexpressing transgenic plant produced by said method shows dwarf phenotypes, such as shorter height multiple shoots, floral shoot internodes, as compared to wild-type plant.

The plant to which the inventive methods can be applied may be a dicotyledonous plant or a monocotyledonous plant. The dicotyledonous plant includes soy bean, *Arabidopsis thaliana*, tobacco plant, eggplant, red pepper, petunia, potato, tomato, Chinese cabbage, rape, cabbage, cotton plant, lettuce, peach, pear, strawberry, watermelon, melon, cucumber, carrot and celery. The monocotyledonous plant includes rice, barley, wheat, rye, corn, sugar cane, oat, and onion.

The PAPP5 according to the present invention is a protein involved in phytochrome signal transduction, which interacts with phytochrome A and phytochrome B. The TPR domain located at the N-terminus of the PAPP5 protein is involved in the interaction between PAPP5 and phytochromes, and the C-terminal domain of the PAPP5 has phosphatase activity. The PAPP5 is activated by autophosphorylated Pfr phytochrome and has the enzymatic activity of dephosphorylating the autophosphorylated phytochrome. Thus, the present invention provides a method of identifying a phytochrome signal transduction-associated substance using the PAPP5 protein, functional equivalents thereof, or polynucleotides encoding the same. The phytochrome signal transduction-associated substance identified by this method may be one having the activity of increasing or inhibiting the activity, expression and/or intracellular level of the inventive polypeptide or a polynucleotide encoding the polypeptide. The substance may be one having the same or similar activity as the inventive polypeptide or polynucleotide. Alternately, the substance may also be one involved in phytochrome signal transduction by interaction with the inventive polypeptide or the polynucleotide encoding the polypeptide. The substance includes, but is not limited to, polynucleotide, polypeptide, chemical or natural extract.

The above method can be performed using the inventive polypeptide or the polynucleotide encoding the same, as a probe. As used herein, the term "probe" refers to a mediator for identifying the desired substance. For example, the above method may be performed by analyzing the binding pattern between a candidate substance and the inventive polypeptide or polynucleotide using the polypeptide or the polynucleotide as a probe. Alternatively, this method may be performed by contacting the inventive PAPP5 with a candidate substance to identify a substance that inhibits or increases the activity of the PAPP5. In this case, the method may comprise the steps of culturing a candidate substance along with recombinant cell expressing the inventive PAPP5, and measuring the effect of the candidate substance on an increase in the activity or intracellular level of the PAPP5.

Alternatively, this method may also be performed by identifying a gene having the same or similar function as the inventive gene from other plants, through hybridization between the inventive polynucleotide or fragment thereof and cDNA prepared from RNA or mRNA extracted from other plants. The method may also be performed by identifying either a substance that binds directly to the polynucleotide or a substance that inhibits or activate the expression of the polynucleotide. In addition, this method may comprise performing a sequence homology search program known in the art using the inventive PAPP5 or polynucleotide encoding the same, so as to identify a protein or gene having high homology with the PAPP5 or polynucleotide encoding the same.

The above identification may be performed by various methods generally used in the art, including, but not limited to, cDNA library screening, BAC (bacterial artificial chromosome) screening, DNA chip, protein chip, polymerase chain reaction (PCR), Northern blot, Southern blot, Western blot, enzyme-linked immunosorbent assay (ELISA), 2-D gel analysis, yeast 2-hybrid system, and in vitro binding assay.

The inventive polypeptide or the polynucleotide encoding the polypeptide may be labeled with radioactive isotope, fluorescent dye or light development enzyme, in order to facilitate the screening and isolation of a substance to be identified. Preferably, it may be labeled with $^{3}H$, $^{32}P$, $^{35}S$, FITC (fluorescein isothiocyanate), TRITC (tetramethylrhodamine isothiocyanate), biotin, digoxigennin, HRP (horse-radish peroxidase), glucose oxidase, alkaline phosphatase, or the like. Labeling methods are known in the art. For example, a nucleic acid may be labeled by a method of uniformly labeling the entire nucleic acid using, for example, nick translation, random oligonucleotide primers, or a method of labeling the 5'- or 3'-terminal region, such as kination or filling-in. Also, a polypeptide may be labeled by radioactive oxonation. The tyrosine or histidine of the polypeptides can be labeled directly with radioiodine. It also may be labeled with Chloramine-T, Iodogen or lactoperoxidase.

Furthermore, the TPR domain of the inventive PAPP5 protein (the sequence of amino acids 1-138 of SEQ ID NO: 4) is involved in the interaction between the PAPP5 and phytochromes, as described above, and if it is overexpressed in plants, it will cause plant dwarfism. It was first found in the present invention that the overexpression of the TPR domain causes dwarfism in plants. Thus, the present invention provides a method of identifying a plant dwarfism-causing substance using the TPR domain or a polynucleotide encoding the same, as a probe. This method allows the identification of a substance that indirectly or directly causes dwarfism in plants either by inducing or promoting the expression of the TPR domain of the inventive PAPP5 protein or by interacting with the TPR domain. The identification may be performed by the above-described methods.

In another aspect, the present invention provides a method of producing a protein having phosphatase activity using the inventive polypeptide or a polynucleotide encoding the polypeptide. This method comprises the step of:

(a) introducing a polynucleotide encoding a polypeptide having either an amino acid sequence of SEQ ID NO: 4 or an amino acid sequence having a homology of at least 70% with said amino acid sequence into an expression vector;

(b) introducing the expression vector into a cell;

(c) culturing the cell to express the polynucleotide; and (d) collecting the cultured protein from the cell culture.

The polynucleotide which can be used in this method includes a polynucleotide encoding an amino acid sequence set forth in SEQ ID NO: 4, and a polynucleotide encoding a polypeptide having an amino acid sequence having a homology of at least 70% with said amino acid sequence. Preferably, a polynucleotide that encodes either a polypeptide of SEQ ID NO: 4 or a polypeptide (SEQ ID NO: 14) with a deletion of amino acids 1-138 of SEQ ID NO: 4 may be used. More preferably, a polynucleotide having a nucleotide sequence of SEQ ID NO: 3 or SEQ ID NO: 15 may be used. In this method, the cell may be a eukaryotic cell, such as yeast, or a prokaryotic cell, such as *E. coli* cell.

In one embodiment of the present invention, in order to identify a new protein interacting with phytochromes, an *Arabidopsis thaliana* cDNA library was screened using a yeast 2-hybrid system. In this case, the full-length cDNA of phytochrome A was used as a bait (FIG. 1). We analyzed deduced amino acid sequences of phytochrome-interacting positive clones resulted from the yeast 2-hybrid screening. As a result, it could be seen that one clone among the clones is a kind of type 5 serine/threonine protein phosphatase (PP5). The N-terminal region of the PP5 protein has 3-4 TPRs (tetratricopeptide repeats), which are implicated in protein-protein interaction (Das, A. K., et al., *EMBO J.,* 17:1192-1199, 1998; Skinner, J. et al., *J. Biol. Chem.,* 272:22464-22471, 1997; Ollendorff, V. et al., *J. Biol. Chem.,* 272:32011-32018, 1998; Chinkers, M. *Trends Endocrinol. Metab.,* 12:28-32, 2001), and a domain containing 3 TPRs was also present in the N-terminal region of the selected positive clone (see FIGS. 2 and 3). Also, the C-terminal region of the selected clone contains the highly conserved phosphatase domain, which contains a motif necessary for serine/threonine phosphatase activity and a sequence (-SAPNC-) whose phosphatase activity is inhibited by binding with an okadaic acid (see FIG. 3). The present inventors named the selected positive clone "PAPP5" (phytochrome-associated protein phosphatase 5).

The analyses of in vivo and in vitro protein-protein interactions showed that the inventive PAPP5 protein interacted specifically with phytochromes (see FIGS. 4 and 5), and in these interactions, the TPR domain at N-terminus of the PAPP5 protein was involved (see FIG. 6). Furthermore, the enzymatic activity of the PAPP5 protein was determined using a general inorganic substrate of phosphatases, para-nitrophenol phosphate ($\rho$-NPP). As a result, it could be seen that the PAPP5 protein has allosteric conformational change-dependent activity. This conformational change was induced by an arachidonic acid in vitro (see FIG. 7), suggesting that TPR domain is an autoinhibitory region.

Moreover, it was found that the PAPP5 protein effectively dephosphorylated the autophosphorylated phytochrome in vitro, and the phosphatase activity was regulated by the wavelength of light (see FIG. 11). Particularly, the dephosphorylation of phytochromes by PAPP5 was strong, mainly in the Pfr phytochrome. The in vivo and in vitro results suggest that the PAPP5 is a regulator of phytochrome-mediated light signalling pathways. Also, the results suggest that the reversible phosphorylation/dephosphorylation of phytochromes in which the PAPP5 protein is involved plays an important role in the biological activity of phytochromes and the regulation of phytochrome-mediated light signal transduction.

In another embodiment, the phosphatase activity of an N-terminus or C-terminus-deleted mutant of the PAPP5 protein was examined, and as a result, it was confirmed that the N-terminus-deleted mutant of the PAPP5 maintained the phosphatase activity intact (see C of FIG. 7).

Since the phosphatase activity of PP5s is known to be promoted by an arachidonic acid (Das, A. K., et al., *EMBO J.,* 17: 1192-1199, 1998; Skinner, J. et al., *J. Biol. Chem.,* 272: 22464-22471, 1997; Ollendorff, V. et al., *J. Biol. Chem.,* 272:32011-32018, 1998; Chinkers, M. *Trends Endocrinol. Metab.,* 12:28-32, 2001), whether the enzymatic activity of the PAPP5 protein is induced by the arachidonic acid was examined. As a result, it could be seen that the phosphatase activity of the full-length PAPP5 was also induced by the arachidonic acid at high level (see FIG. C of FIG. 7). Meanwhile, the N-terminus-deleted mutant of the PAPP5 protein showed an equal or higher activity than the arachidonic acid-induced phosphatase activity of the PAPP5 protein, and the activity was independent of arachidonic acid.

In still another embodiment of the present invention, a knock-out mutant of PAPP5 and a PAPP5-overexpressing plant were produced and examined for their Rc-HIR and FRc-HIR phenotypes. As a result, the knock-out mutant of PAPP5 showed a long hypocotyl phenotype in contrast with the PAPP5-overexpressing phenotype (see FIG. 9), and also diminished rates of light-induced hook opening and cotyledon separation, reduced cotyledon expansion, and early flowering (data not shown). On the other hand, the PAPP5-overexpressing plant showed a shorter hypocotyl phenotype than that of a wild-type plant (see FIG. 9). It also strongly showed an "end-of-day far-red" (EOD-FR) response that is a phytochrome B-mediated response, and anthocyanin accumulation that is a phytochrome A-mediated response (date not shown), as compared with those of a wild-type plant. Such results indicate that the PAPP5 protein functions as a positive regulator in phytochrome A and phytochrome B signaling pathways.

In yet another embodiment of the present invention, in order to further examine the roles of the TPR domain of PAPP5, a reverse genetic approach with dominant negative mutation was used. For this purpose, the TPR domain of PAPP5 (a polypeptide consisting of the sequence of amino acids 1-138 of SEQ ID NO: 4) was overexpressed in wild-type plants. As a result, the TPR domain-overexpressed plants showed phenotypes similar to those caused by gibberellin deficiency, and also dwarf phenotypes, including short height, multiple shoots and floral shoot internodes.

BRIEF DESCRIPTION OF THE DRAWINGS

FIG. 3 shows the results of multiple alignment of the amino acid sequences of the inventive PAPP5 protein (SEQ ID NO: 16) and type 5 serine/threonine protein phosphatases isolated from several species.

H. sap PP5: *Homo sapiens* PP5 (GenBank accession No. CAA61595) (SEQ ID NO: 17);
M. mus PP5: *Mus musculus* PP5 (GenBank accession No. AAB70573) (SEQ ID NO: 18);
R. nor PP5: *Rattus norvegicus* PP5 (GenBank accession No. CAA54454) SEQ ID NO: 19;
S. cer PP5: *Saccharomyces cerevisiae* PP5 (GenBank accession No. CAA58158) (SEQ ID NO: 20);
D. meg PP5: *Drosophila melanogaster* PP5 (GenBank accession No. CAB99478) (SEQ ID NO: 21); and
C. ele PP5: *Caenorhabditis elegans* PP5 (GenBank accession No. CAC51076) (SEQ ID NO: 22).

Figure 4:
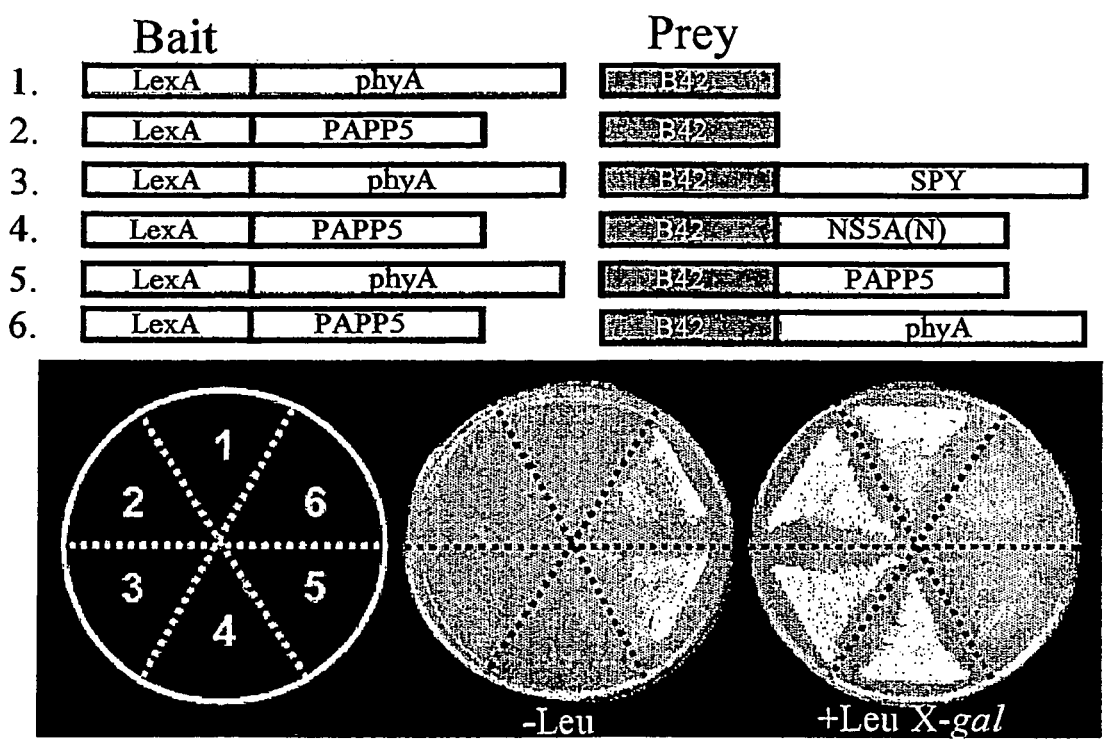

FIG. 4 shows the constructions of each of a bait and prey used in yeast 2-hybrid analysis to examine the interaction between the inventive PAPP5 and phytochrome A, and the results of the yeast 2-hybrid analysis using the bait and the prey.

Figure 5:
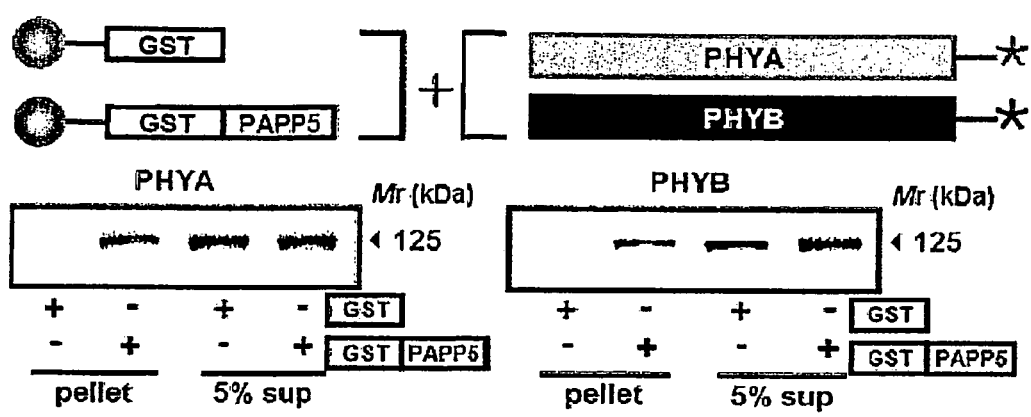

FIG. 5 shows the results of in vitro binding assay conducted to examine the interaction between a fusion protein (GST-PAPP5) of gluthathione-5-transferase (GST) and PAPP5, and phytochrome A or phytochrome B.

Figure 6:
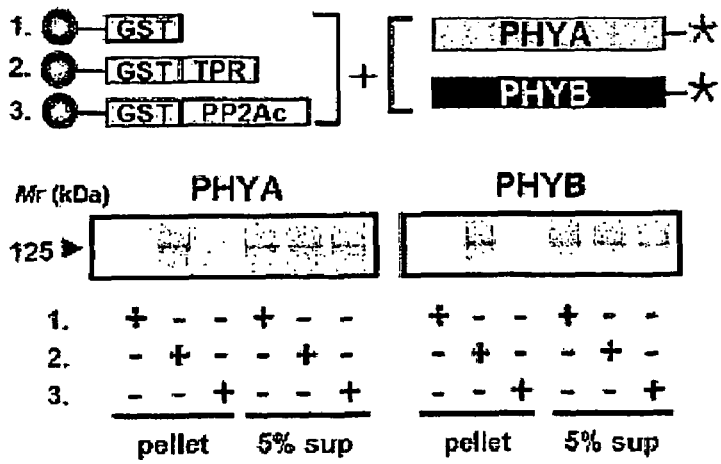
Figure 6:
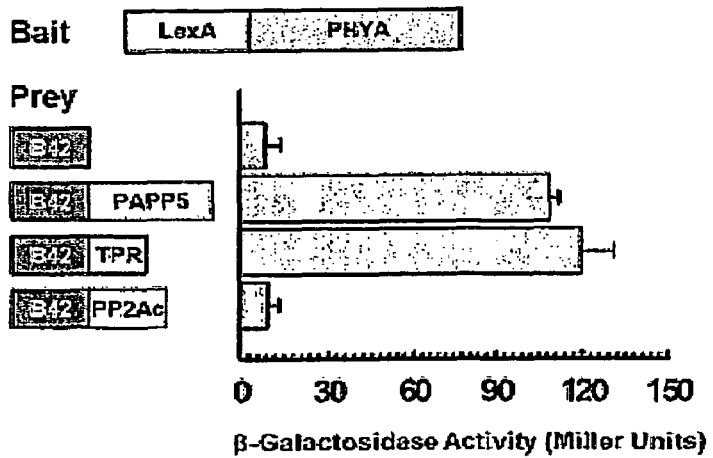
Figure 6:
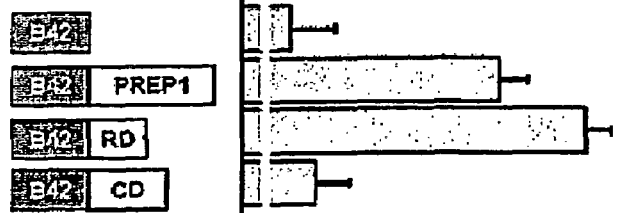

FIG. 6 shows the results of pull-down analysis conducted to identify a region interacting with phytochromes in the inventive PAPP5 protein (A), and the results of quantitative yeast 2-hybrid interaction assay using fragments of PAPP5.

Figure 7:
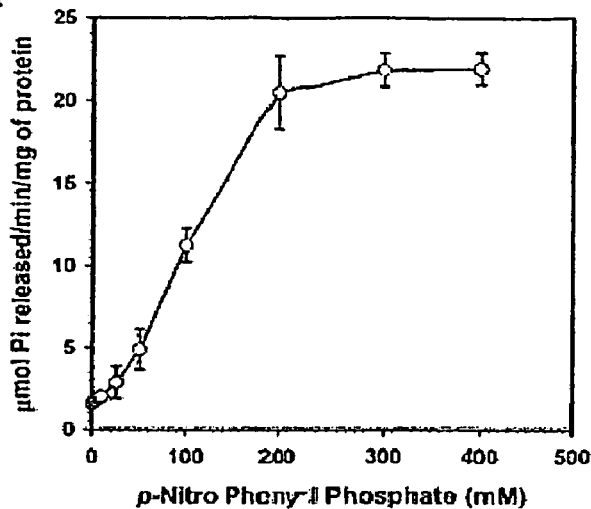
Figure 7:
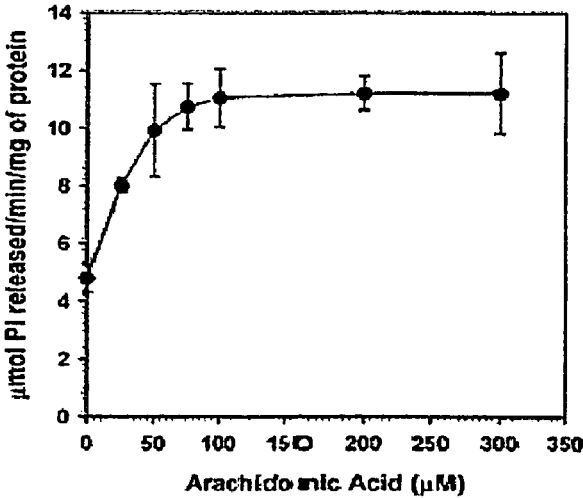
Figure 7:
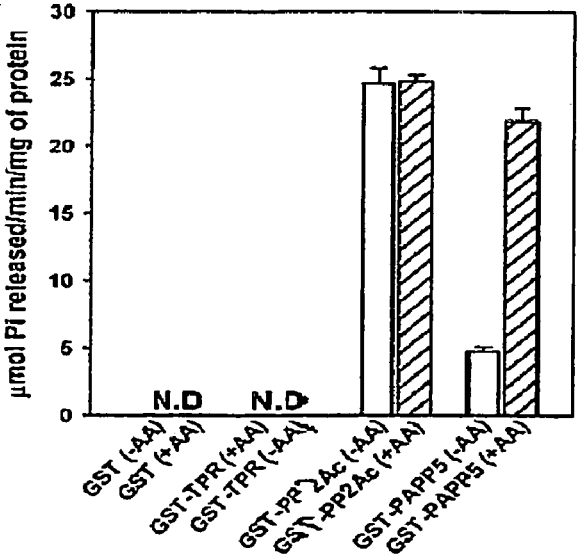

FIG. 7 shows the results of in vitro phosphatase assay conducted to examine the enzymatic activity of the inventive PAPP5 protein.

A: results of analysis conducted using ρ-nitrophenol phosphate (ρNPP) as a substrate at an arachidonic acid concentration of 100 µM;

B: analysis results for catalytic effects caused by the addition of arachidonic acid at a ρ-NPP concentration of 100 mM; and C: analysis results for enzymatic activities of PAPP5 and its domain fragments caused by the addition of arachidonic acid.

Figure 8:
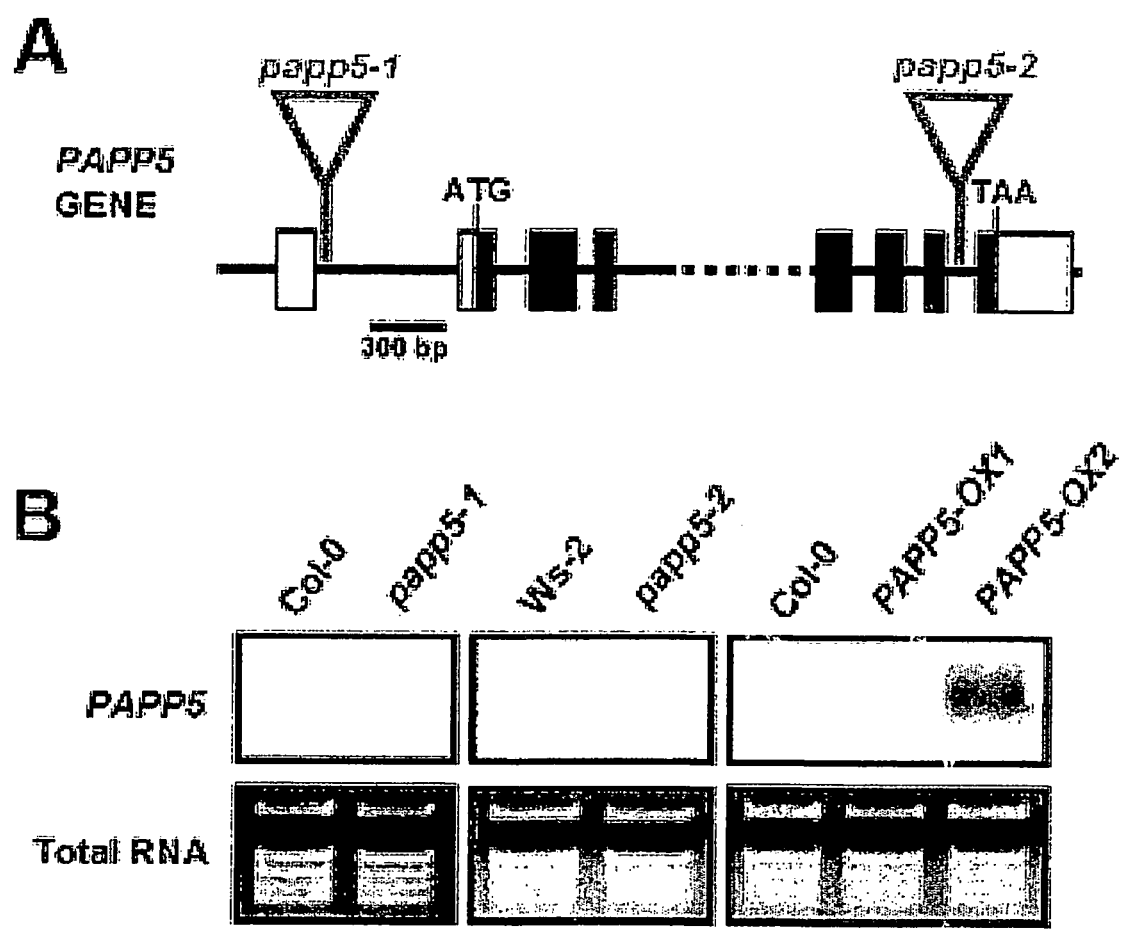

FIG. 8 is a schematic diagram showing an insertion of T-DNA in PAPP5 gene-knock out mutants (papp5-1 and papp5-2) (A), and the result showing the expression level of the PAPP5 gene in the knock-out mutants, as compared to those in wild-type plants (Col-0, Ws-2) and PAPP5-overexpressing plants (PAPP5-OX1 and PAPP5-OX2) (B).

Figure 9:
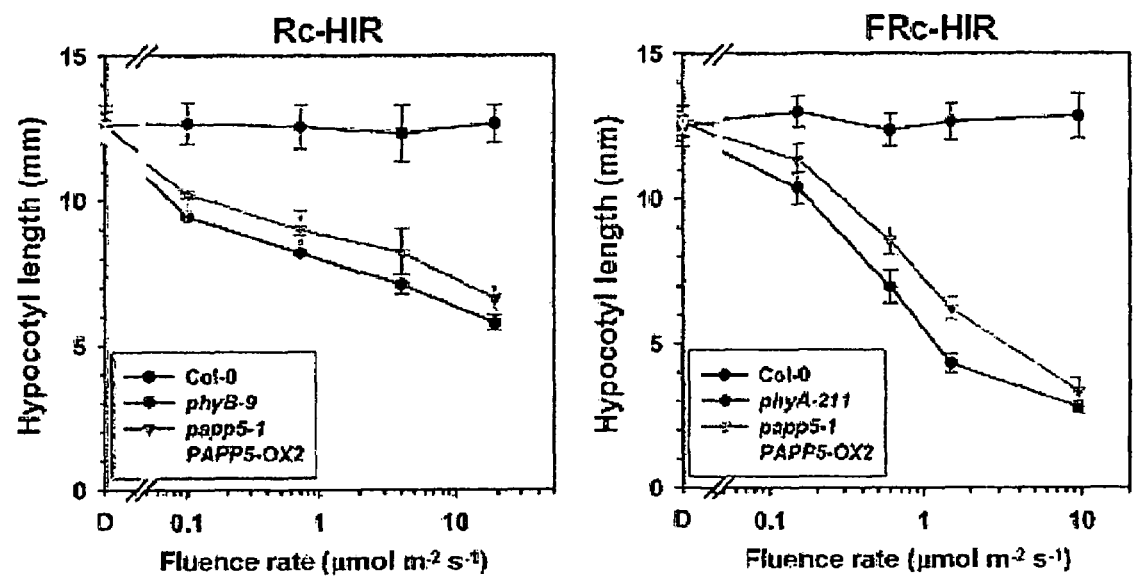

FIG. 9 shows the results of measurement for the photoresponsiveness of a knock-out mutant (papp5-1) and an PAPP5-overexpressing plant (PAPP5-OX2), as compared to a wild-type plant (Col-0) and phythochrome mutants (phyA-211 and phyB-9).

Rc-HIR: red light irradiation.
FRc-HIR: far-red-light irradiation.

Figure 10:
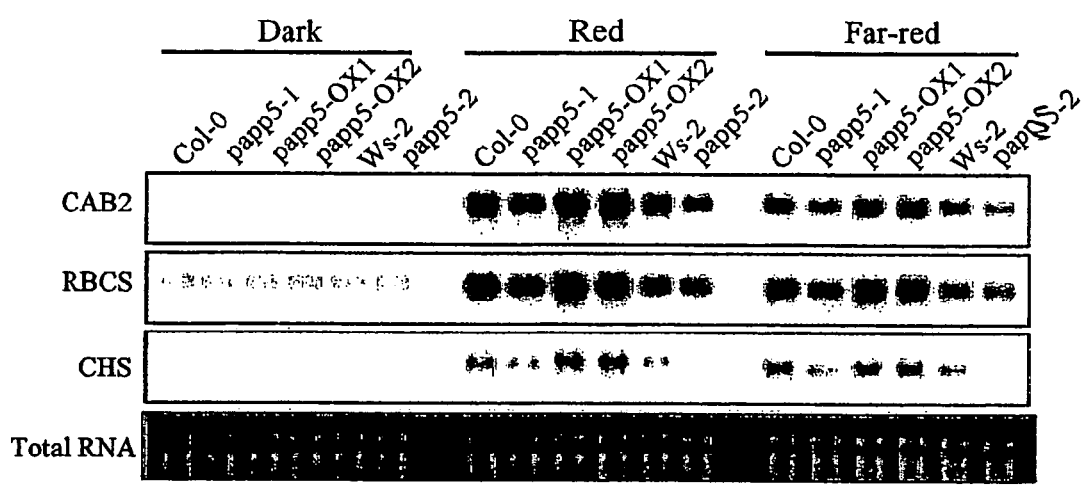

FIG. 10 shows the results of analysis for the expression levels of photoresponsive genes (CAB2, RBCS and CHS) in knock-out mutants (papp5-1 and papp5-2) and PAPP5-overexpressing plants (PAPP5-OX1 and PAPP5-OX2) upon red light or far-red-light irradiation, as compared to those in wild-type plants (Col-0 and Ws-2).

Figure 11:
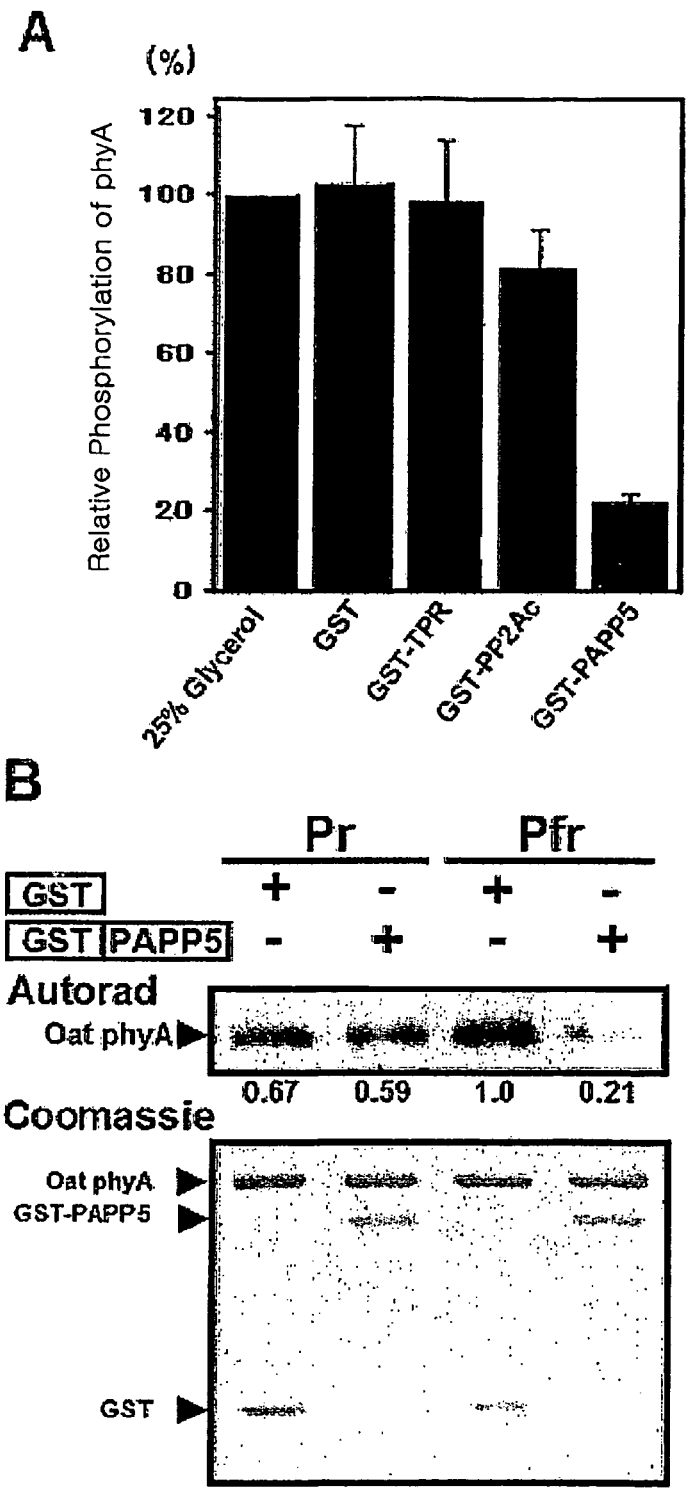

FIG. 11 shows the results of measurement of the dephosphorylation activity of PAPP5 on autophosphorylated oat phytochrome A (phyA).

A: results of measurement of dephosphorylation activity of PAPP5 and its domain fragments;
25% glycerol and GST: control groups;
GST-TPR: a fusion protein of GST and TPR domain of PAPP5;
GST-PP2Ac: a fusion protein of GST and catalytic domain having similarity with type 2A phosphatase of PAPP5 (PP2A)
GST-PAPP5: a fusion protein of GST and full-length PAPP5

B: measurement results for dephosphorylation activity of PAPP5 according to light absorption pattern of oat phytochrome A.

Figure 12:
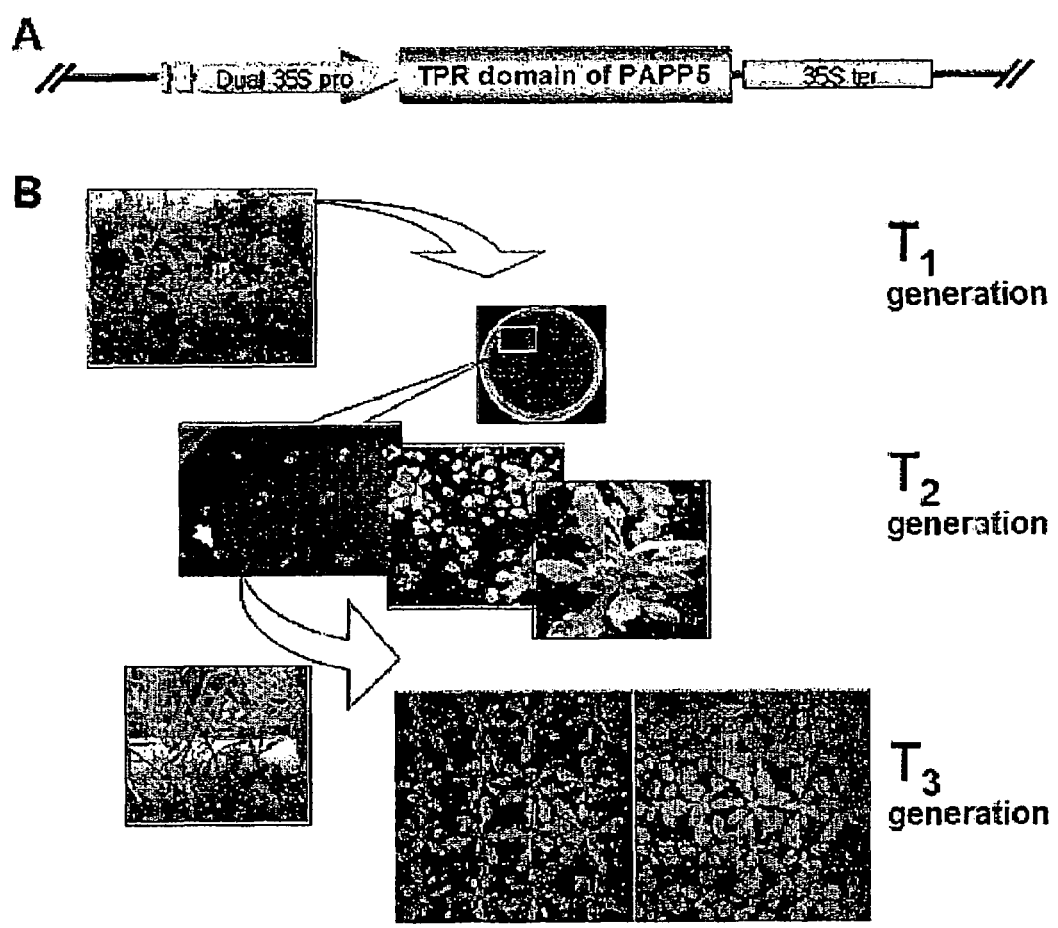

FIG. 12 shows the schematic construction of a vector overexpressing the TPR domain of PAPP5 (A), and the appearance of $T_1$, $T_2$ and $T_3$ generations of TPR domain-overexpressing plants introduced with the vector (B).

BEST MODE FOR CARRYING OUT THE INVENTION

The present invention will be described in detail by examples. It is to be understood, however, that these examples are provided for illustrative purpose only and are not construed to limit the scope of the present invention.

Example 1

Yeast Two-Hybrid Screening

Figure 1:
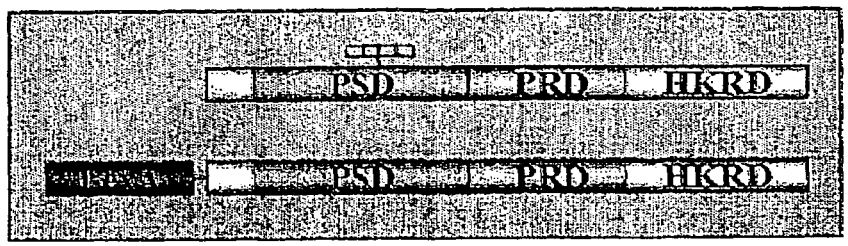
FIG. 1 is a schematic diagram of a bait for yeast 2-hybrid system, constructed to select a phytochrome A-interacting protein from the *Arabidopsis thaliana* cDNA library.
partitioned rectangle: chromophore
PSD: photosensory domain
PRD: PAS (Per-Arnt-Sim)-associated domain
HKRD: histidine kinase-associated domain FIG. 2 schematically shows a PAPP5 gene in the *Arabidopsis thaliana* genome and a PAPP5 protein encoded from the gene.

The present inventors used the yeast-2 hybrid system (DupLEX-A™, OriGene Technologies) to search for proteins binding to phytochromes. First, a cDNA library was prepared from 3-week-old *Arabidopsis thaliana* according to any method known in the art. Each of cDNA fragments was inserted into a pJG4-5 plasmid (OriGene Technologies) (preparation of a prey). Meanwhile, a bait was constructed by linking phytochrome A gene PHYA to the LexA-DNA binding domain of pGilda (OriGene Technologies) (see FIG. 1). For this purpose, a phytochrome A gene was cloned using primers of SEQ ID NO: 1 and SEQ ID NO: 2 from a PHYA cDNA clone provided by Dr. Joanne Chory, Salk Institute for Biological Studies, San Diego, USA. At this time, the PCR reaction consisted of predenaturation of template DNA for 5 min at 94° C., and then, 35 cycles of 30 sec at 94° C., 30 sec at 50° C. and 2 min and 30 sec at 72° C., followed by 15 min at 72° C. Thereafter, an EGY48 yeast reporter strain (OriGene Technologies) introduced with a pSH18-34 reporter plasmid was co-transformed with the *Arabidopsis thaliana* cDNA fragment-containing prey and the PHYA gene-containing bait. A total of $7 \times 10^6$ colonies were screened, and as a result, about 150 colonies showing a positive signal to Leu- and β-galactosidase were obtained.

Example 2

Analysis of Nucleotide Sequences of Positive Clones

Figure 2:
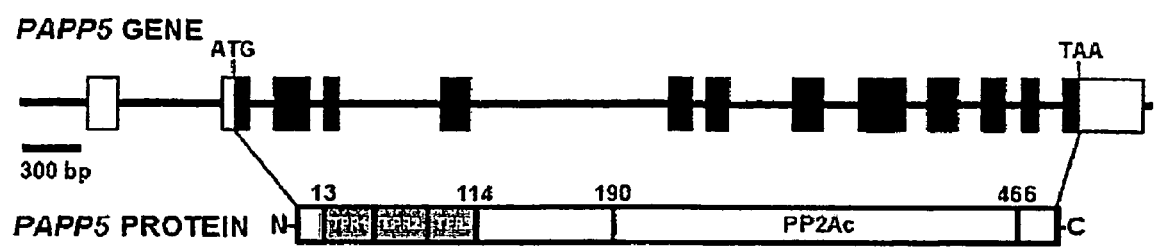
Figure 3:
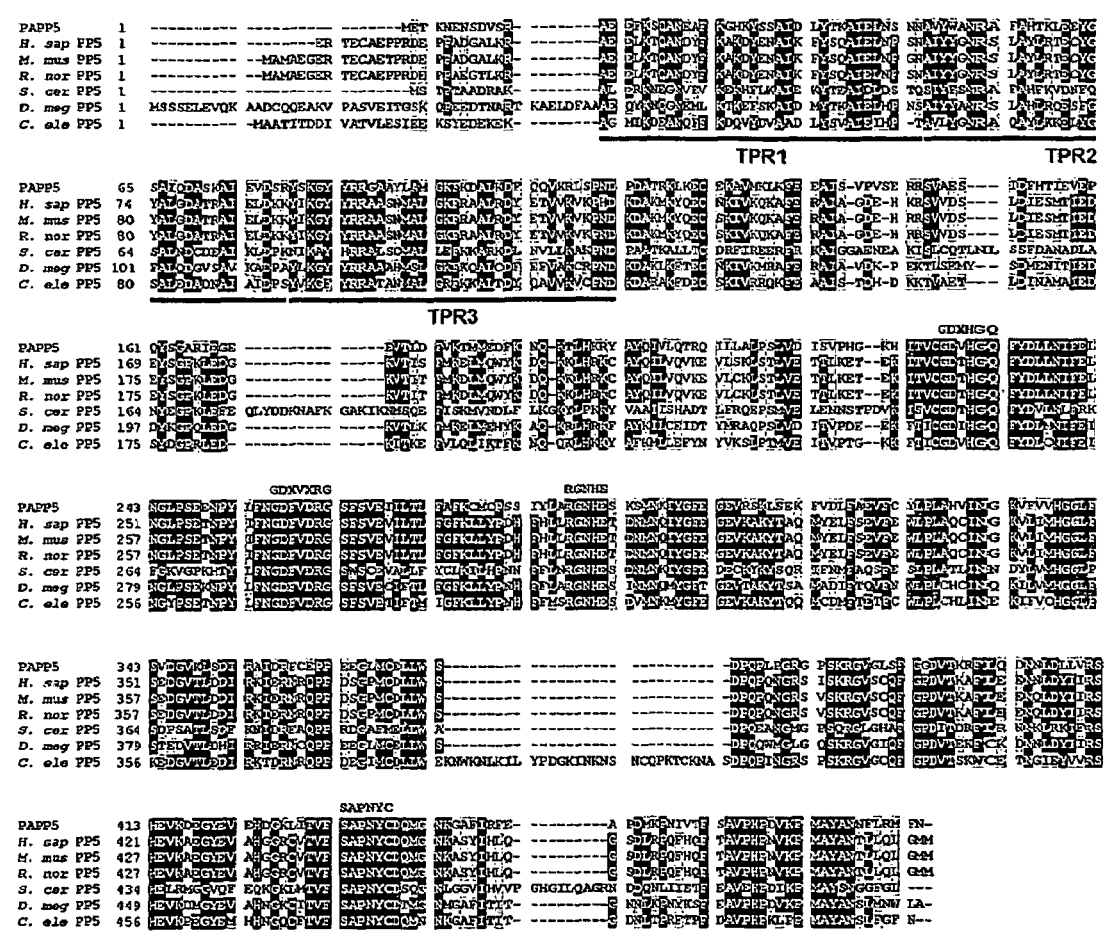

From the positive clones obtained in the yeast 2-hybride screening of Example 1, plasmids were isolated and then, the nucleotide sequence of each of the cDNA clones was determined. Next, homology searching was performed using the *Arabidopsis thaliana* genome database. As a result, it was found that one of the cDNA clones shows a homology with the sequences in BAC clones F14N22 and F7D19 on chromosome 2. The sequence analysis of the cDNA clone revealed that 13 exons and 12 introns existed in the coding region of the cDNA clone (see FIG. 2), and an open reading frame (ORF) encoding 484 amino acids was included. Also, its molecular weight was estimated to be 54 kDa. The deduced amino acid sequence was analyzed by NCBI BLAST, and as a result, a protein encoded from the cDNA clone showed high homology with type 5 serine/threonine protein phosphatases (PP5s) from other several species. The amino acid sequence of the protein was subjected to pairwise alignment with other several PP5s (see FIG. 3), and as a result, the overall identity was 50-57%, and the C-terminal catalytic domain showed a homology of 54-62% which is slightly higher than the overall identity. However, the similarity of the amino acid sequences was very high (more than 70%).

Meanwhile, the results of PROSITE analysis revealed that TPR (tetratricopeptide repeat) which have been found in all PP5s by this time existed in the N-terminal region of the protein. Moreover, the C-terminal region of the protein contains a highly conserved type 2A serine/threonine protein phosphatase domain (PP2A), within which motifs (-GDXHGQ- [SEQ ID NO: 23], -GDXVXRG- [SEQ ID NO: 24] and -RGNHE- [SEQ ID NO: 25]) necessary for the activity of serine/threonine phosphatase were included (see FIG. 3). The three conserved motifs play important roles in catalysis, substrate binding and metal ion binding (Ollendorff, V. et al., *J. Biol. Chem.*, 272:32011-32018, 1998). In addition, the C-terminal region of the protein included consensus sequence "SAPNYC" (SEQ ID NO: 26) (Ollendorff, V. et al., *J. Biol. Chem.*, 272:32011-32018, 1998) that binds to an okadaic acid, thereby inhibiting enzyme activity (see FIG. 3). From the above results, it could be found that the cDNA clone encodes a serine/threonine protein phosphatase.

The present inventors named the cDNA clone "PAPP5" (phytochrome-associated protein phosphatase 5). The full-length cDNA sequence of PAPP5 and an amino acid sequence deduced therefrom are set forth in SEQ ID NO: 3 and SEQ ID NO: 4, respectively.

Meanwhile, the results of Northern blot analysis revealed that cDNA of PAPP5 is similar to a single transcript having a total length of about 2 kb, and the result of Southern blot analysis confirmed that PAPP5 is a single copy gene (data not shown).

Example 3

Examination of Molecular Specificity of Interaction Between PAPP5 and Phytochromes A pGilda vector and a pJG4-5 vector (OriGene Technologies) were used to prepare a prey and a bait, respectively (see FIG. 4). In this case, as control groups to examine specific binding, hepatitis C virus (HCV) protein NS5A(N) (distributed from professor S K Jang, Department of Life Science, Pohang University of Science and Technology, Korea) and another plant protein SPINDLY(SPY) having the TPR domain (Jacobsen, S. E., et al., *Proc. Natl. Acad. Sci. U.S.A.* 93:9292-9296, 1996) were used. Furthermore, the prey and the bait were interchanged to observe protein-protein binding by a reciprocal method. The prepared prey and bait together with a pSH18-34 reporter plasmid (OriGene Technologies) were co-introduced into an EGY48 yeast strain (OriGene Technologies). Next, the transformants were selected on a media containing X-gal (5-bromo-4-chloro-3-indolyl-β-D-galactopyranoside; Rose Scientific Ltd.). Plate-growth assays were performed on Leu-drop out media and X-gal media.

As a result, it could be seen that PAPP5 did not interact with the NS5A(N) protein of HCV whereas it interacted specifically with *Arabidopsis thaliana* phytochrome A (see FIG. 4). In addition, another plant protein SPY having the TPR domain did not interact with the phytochrome. This suggests that the binding between PAPP5 and phytochromes is a very specific binding.

Example 4

In Vitro Binding Assay

<4-1> Expression and Purification of GST-PAPP5 Fusion Protein

In order to examine the in vitro interaction between PAPP5 and phytochromes, a vector for expressing a full-length PAPP5 was constructed using a pGEX4T-1 vector (Amersham Pharmacia Biotech.). First, the full-length PAPP5 was amplified by PCR using primers set forth in SEQ ID NO: 5 and SEQ ID NO: 6. The PCR reaction consisted of predenaturation of template DNA for 5 min at 94° C., and then, 30 cycles of 30 sec at 94° C., 30 sec at 50° C. and 1 min at 72° C., followed by 10 min at 72° C. The PCR product was cloned into a pGEX4T-1 vector (Amersham Pharmacia Biotech.). The recombinant vector containing PAPP5 was introduced into *E. coli* BL21. The transformants were cultured with 1 mM IPTG to express a GST-PAPP5 fusion protein. The expressed GST-PAPP5 fusion protein was purified using glutathione-sepharose 4B beads (Amersham Pharmacia Biotech) (Skinner, J. et al., *J. Biol. Chem.*, 272:22464-22471, 1997). In order to purify the protein to a native state, the GST-PAPP5 fusion protein was eluted with a buffer solution containing 50 mM Tris-HCl (pH8.0), 4 mM $MnCl_2$, 0.1% β-mercaptoethanol and 10 mM glutathione. Then, it was dialyzed with a solution containing 25% glycerol, 1 mM EGTA, 0.1% β-mercaptoethanol, 20 mM Tris-HCl (pH7.6) and 4 mM $MgCl_2$, at 4° C. overnight. The dialyzed protein sample was stored at −20° C. until use for analysis.

<4-2> Construction of PHYA and PHYB Expression Vectors

An in vitro transcription/translation system was used to express apoproteins PHYA and PHYB of *Arabidopsis thaliana* phytochromes A and B.

First, in order to synthesize PHYA in vitro, the full-length cDNA of PHYA containing BamHI and XhoI restriction enzyme recognition sequences at both the ends was amplified by PCR using primers set forth in SEQ ID NO: 7 and SEQ ID NO: 2. The PCR reaction consisted of predenaturation of template DNA for 5 min at 94° C., and then, 30 cycles of 30 sec at 94° C., 30 sec at 50° C. and 2 min and 30 sec at 72° C., followed by 10 min at 72° C. Thereafter, the PCR product was inserted into the BamHI-XhoI site of a pTriEx-1 vector (Novagen), thus preparing a recombinant expression vector for the expression of PHYA. Meanwhile, for the synthesis of PHYB, a PCR product having the sequence of FbaI-full length PHYB cDNA-Eco52I was amplified using primers set forth in SEQ ID NO: 8 and SEQ ID NO: 9. This PCR product was inserted into the BamHI-XhoI site of a pTriEx-1 vector, thus preparing a recombinant expression vector for the expression of PHYB. Each of the encoded proteins was synthesized in vitro using $^{35}$S-labeled methionine. The synthesis was performed using a reticulocyte TnT transcription/translation system (Promega) according to the manufacturer's recommendation.

<4-3> In Vitro Binding Assay

1 μg of the GST-PAPP5 fusion protein prepared in Example <4-1> and 10 μl of each of the TnT proteins prepared in Example <4-2> together with a protease inhibitor (Complete, Roche Diagnostics GmbH) were added to a 0.3 ml of binding buffer solution (20 mM Tris-HCl, pH7.5, 150 mN NaCl, 1 mM dithiothreitol, 0.1% Tween 20). Then, the mixture was shaken weakly at 4° C. to induce a binding reaction. After adding 10 μl of glutathione-sepharose 4B beads (Amersham Pharmacia Biotech. AB) to the mixture, the reaction was further performed for one hour in the same condition. After centrifugation, the supernatant fraction was separately stored, and the pellet (sepharose bead fraction) was washed three times with 1 ml of binding buffer solution. The pellet and supernatant fractions were analyzed on 10% acrylamide-containing SDS-PAGE gel. Next, visualization was performed using Fuji FLA-2000R image analyzer (Fuji Photo Film).

As a result, it could be seen that PAPP5 has the property of binding to the phytochromes A and B of *Arabidopsis thaliana* (see FIG. 5).

Example 5

Examination of Interaction Between TPR Domain of PAPP5 and Phytochromes

PP5s comprising the inventive PAPP5 protein are distinguished from other members of the PP1/PP2 group in that they contain a unique N-terminal domain consisting of several TPRs. TPR motifs are assumed to form amphipathic helices and known to mediate protein-protein interaction (Das, A. K., et al., *EMBO J.*, 17:1192-1199, 1998; Skinner, J. et al., *J. Biol. Chem.*, 272:22464-22471, 1997; Ollendorff, V. et al., *J. Biol. Chem.*, 272:32011-32018, 1998; Chinkers, M. *Trends Endocrinol. Metab.*, 12:28-32, 2001). Thus, in order to examine whether TPRs are involved in the interaction between the inventive PAPP5 protein and the phytochrome molecules, a pull-down assay and a quantitative yeast 2-hybrid interaction assay were performed.

<5-1> Pull-Down Assay

According to the same method as in Example <4-1>, each of recombinant expression vectors for the TPR domain of PAPP5 consisting of the sequence of amino acids 1-138 of SEQ ID NO: 4 (N-terminal domain; GST-TPR) and for the PP2A enzymatic domain of PAPP5 with a deletion of amino acids 1-138 in SEQ ID NO: 4 (C-terminal domain; GST-PP2Ac) was constructed using the pGEX4T-1 vector (Amersham Pharmacia Biotech). The TPR domain of PAPP5 was amplified by PCR using primers set forth in SEQ ID NO: 5 and SEQ ID NO: 10. The PCR reaction consisted of predenaturation of template DNA for 5 min at 94° C., and then, 30 cycles of 30 sec at 94° C., 30 sec at 50° C. and 1 min at 72° C., followed by 10 min at 72° C. Meanwhile, the PP2A catalytic domain of PAPP5 was amplified by PCR using primers set forth in SEQ ID NO: 6 and SEQ ID NO: 11. This PCR reaction consisted of predenaturation of template DNA for 5 min at 94° C., and then, 30 cycles of 30 sec at 94° C., 30 sec at 50° C. and 1 min at 72° C., followed by 10 min at 72° C. Thereafter, according to the same method as in Example <4-1>, an in vitro assay was performed on each of the proteins which have been expressed and purified in *E. coli*.

As a result, as shown in FIG. 6A, it was found that only the TPR domain of PAPP5 fused with GST (GST-TPR) has the ability to interact with the phytochrome molecules. This indicates that the TPR domain is involved in the interaction between PAPP5 and phytochrome molecules.

<5-2> Quantitative Yeast Two-Hybrid Assay

In order to quantitatively assay the interaction between the TPR domain of PAPP5 and phytochromes, each of recombinant vectors (preys) for the TPR domain of PAPP5 and for the PP2A catalytic domain of PAPP5 were prepared, respectively.

A PHYA gene or a PHYB gene was prepared by performing PCR according to the same method as in Example <4-2>, and inserted into a pGilda vector. The recombinant vector was used as a bait. The prepared bait or prey was co-introduced into an EGY48 yeast strain together with a pSH18-34 reporter plasmid. The transformed strain was cultured until the $OD_{600}$ value reached about 0.7. The cultured cells were washed one time with Z-buffer solution (60 mM $Na_2HPO_4$, 40 mM $NaH_2PO_4$, 10 mM KCl, 1 mM $MgSO_4$, pH 7.0), and then re-suspended in the solution. Thereafter, the solution was frozen with liquid $N_2$. The frozen solution was dissolved, to which β-mercaptoethanol and ONPG (o-nitrophenyl-β-D-galactopyranoside) were then added at final concentrations of 0.2% and 0.67 mg/ml, respectively. The dissolved solution was allowed to react for 30 minutes at 37° C. Next, $Na_2CO_3$ was added to the solution at a final concentration of 0.3 M to terminate the reaction. The absorbance at 0.420 nm was measured, and the β-galactosidase activity was determined in Miller units (Miller, J. H. *Experiments in Molecular Genetics* (Cold Spring Harbor Laboratory, Cold Spring harbor, N.Y., 1972)).

As a result, as shown in FIG. 6B, the TPR domain-deleted PP2A catalytic domain of PAPP5 (B42-PP2Ac) showed a remarkable reduction in the activity of interaction with phytochromes. This result reconfirms that the TPR domain of PAPP5 is a specific region for the interaction between PAPP5 and phytochrome molecules. Also, this coincides with the result of the pull-down assay.

Example 6

In Vitro Phosphatase Assay

<6-1> Measurement of Phosphatase Activity

In order to examine whether the inventive PAPP5 protein has enzymatic activity, an enzymatic assay was performed using inorganic p-nitrophenyl phosphate (pNPP) as a substrate. First, the GST-PAPP5 fusion protein purified in Example <4-1> was prewarmed at 30° C. for 1 minute. The prewarmed enzyme solution was added to 100 μl of kinase/phosphatase (KP) buffer (20 mM Tris-HCl pH 7.5, 30 mM MgCl$_2$, 1 mM EDTA, 1 mM EGTA, 0.1% β-mercaptoethanol, 0.1% ethanol) containing O-400 mM ρNPP to initiate a reaction. To examine the autohydrolysis of ρNPP at each substrate concentration, the GST-PAPP5 enzyme solution was not added to a control group. After reaction at 30° C. for 15 minutes, 900 μl of 0.25N NaOH was added to terminate the reaction. The absorbance at 410 nm was measured. After subtracting the absorbance value of the control reaction solution containing all the components except for the enzyme from that of the reaction solution containing the enzyme, the rate was calculated using a millimolar extinction coefficient (17.8) of ρ-nitrophenolate ions.

As a result, as shown in FIG. 7A, it could be seen that the phosphatase activity was increased with an increase in the concentration of ρNPP. This indicates that the inventive PAPP5 protein has phosphatase activity. A an enzyme-substrate reaction in the presence of 100 μM arachidonic acid was calculated as a Km and Vmax of Michaelis-Menten kinetic, and as a result, Km was 160 mM ρNPP and Vmax was 22 μmmol Pi released/min/mg.

<6-2> Measurement of Induction of Catalytic Activity of PAPP5 by Arachidonic Acid The most distinguishable characteristic of PP5s is that their catalytic activity is induced by arachidonic acid (Das, A. K., et al., *EMBO J.*, 17:1192-1199, 1998; Skinner, J. et al., *J. Biol. Chem.*, 272:22464-22471, 1997; Ollendorff, V. et al., *J. Biol. Chem.*, 272:32011-32018, 1998; Chinkers, M. *Trends Endocrinol. Metab.*, 12:28-32, 2001). In order to confirm if the phosphatase activity of the inventive PAPP5 protein is activated by arachidonic acid, 0-300 μM arachidonic acid was added to a reaction mixture in the presence of 100 mM ρNPP, and the enzymatic activity was measured according to the same method as Example <6-1>.

As a result, the activity of GST-PAPP5 was increased in a concentration-dependent manner by arachidonic acid, and reached the stationary phase at concentration above about 100 μM of an arachidonic acid (see FIG. 7B).

Furthermore, the catalytic activity of PP5s is known to be inhibited by okadaic acid in vitro (Das, A. K., et al., *EMBO J.*, 17:1192-1199, 1998; Skinner, J. et al., *J. Biol. Chem.*, 272: 22464-22471, 1997; Ollendorff, V. et al., *J. Biol. Chem.*, 272:32011-32018, 1998; Chinkers, M. *Trends Endocrinol. Metab.*, 12:28-32, 2001). Thus, the inhibitory effect of okadaic acid on the phosphatase activity of GST-PAPP5 was examined. As a result, the IC$_{50}$ of okadaic acid, at which the enzyme activity is inhibited by 50%, was 5 nM (data not shown).

These results demonstrate that the inventive PAPP5 encodes a protein belonging to the PP5 subfamily of the serine/threonine protein phosphatase family.

<6-3> Examination of Enzymatic Activity by Allosteric Conformational Structure Change The results of previous studies on PP5s isolated from other species revealed that the N-terminal fragment of PP5s, which contains TPR motifs, shows an allosteric conformational change (Das, A. K., et al., *EMBO J.*, 17:1192-1199, 1998; Skinner, J. et al., *J. Biol. Chem.*, 272:22464-22471, 1997; Ollendorff, V. et al., *J. Biol. Chem.* 272:32011-32018, 1998; Chinkers, M. *Trends Endocrinol. Metab.*, 12:28-32, 2001). Thus, in order to confirm if PAPP5 also have this property, the present inventors examined the phosphatase activities of GST-PAPP5, GST-TPR and GST-PP2Ac in the same manner as in Example <6-1>. At this time, the concentration of ρNPP was 100 mM.

As a result, as shown in FIG. 7c, it could be seen that the phosphatase activity of GST-PAPP5 was about five times increased by arachidonic acid. On the other hand, GST-PP2Ac with a deletion of the TPR domain (amino acids 1-138) showed five times higher activity than that of GST-PAPP5 with no arachidonic acid, regardless of the addition of arachidonic acid.

These results indicate that the phosphatase activity of PAPP5 undergoes regulation by the allosteric conformational change of the TPR domain, similarly to other PP5s, while the TPR domain also has an autoinhibitory activity. Also, these results suggest that the TPR domain-deleted PP2A catalytic domain of PAPP5 can be used as a phosphatase.

Example 7

Examination of Plant Phenotypes by Inactivation or Overexpression of PAPP5

In order to examine whether PAPP5 is involved directly in phytochrome-mediated light signal transduction in vivo, a knock-out mutant of a PAPP5 gene and a PAPP5-overexpressing plant were produced and examined for their phenotypes.

<7-1> Screening of Knock-Out Mutants of PAPP5 Gene

Two mutants carrying a T-DNA insertion within the PAPP5 gene were identified to establish two mutant lines (papp5-1 and papp5-2).

One mutant papp5-1 was obtained from a separate T-DNA mutagenized population (SIGnAL T-DNA Express, Salk Institute Genomic Analysis Laboratory) prepared from Col-0 wild-type plants. The T-DNA in the mutant was found to be inserted into 1$^{st}$ intron (see FIG. 8A), and from this fact, papp5-1 was assumed as a null allele. Another mutant papp5-2 was isolated by screening DNAs isolated from a knock-out mutant population (Krysan, P. J., etat., *Plant Cell*, 11:2283-2290, 1999) prepared from Ws-2 wild-type plants. The T-DNA in papp5-2 was found to be inserted into 12nd intron (see FIG. 8A).

Segregation examination using drug-resistant markers (kanamycin-resistant genes) was conducted, and the results showed that both papp5-1 and papp5-2 had single T-DNA inserted into the PAPP5 locus. Several drug-resistant seedlings for the two mutant lines having the null allele were propagated. Then, homozygous lines were identified by screening for the drug resistance in the progeny of individual plant. The homozygosities of the mutant lines were confirmed either by Southern blot analysis or PCR (data not shown).

<7-2> Construction of PAPP5-Overexpressing Plants

PAPP5 cDNA was amplified by PCR using primers set forth in SEQ ID NO: 12 and SEQ ID NO: 13. The PCR reaction consisted of predenaturation of template DNA for 5 min at 94° C., and then, 30 cycles of 30 sec at 94° C., 30 sec at 50° C. and 1 min at 72° C., followed by 10 min at 72° C. Thereafter, the PCR product was cloned into a pNB96 vector having a dual 35S CaMV promoter and followed by a 35S CaMV terminator (35S ter). The recombinant vector was introduced into *Agrobacterium* strain AGL1 by electroporation. Next, according to the floral-dip method (Clough, S. J. & Bent, A. F. *Plant J.*, 16:735-743, 1998), *Arabidopsis thaliana* was transformed with the transformed *Agrobacterium*. 25 μg/ml of DL-PPT (DL-phosphinothricin, Duchefa Biochemie BV) was used to select two independent transgenic plants overexpressing PAPP5. The two selected plants were named "PAPP5-OX1" and "PAPP5-OX2", respectively.

<7-3> Confirmation and Analysis of Knock-Out Mutants and Overexpression Plants a) Northern Blot Analysis For analysis of PAPP5 transcript levels, total RNA from the plants obtained in Examples <7-1> and <7-2> was isolated using RNeasy plant mini kits (Qiagen, Valencia, Calif.). 10 µg of the total RNA was separated on 1.0% agarose gel containing formaldehyde, and subsequently transferred to a nylon membrane. The membrane was hybridized with a $^{32}$P-labeled probe specific to PAPP5 gene (the 300-700 bp fragment of SEQ ID NO: 3). The radioactive signals were quantified by Fuji FLA-2000R image analyzer (Fuji photo film).

As a result, as shown in FIG. 8B, the radioactive signals were not detected in the knock-out mutants papp5-1 and papp5-2 whereas it was detected in the overexpression plants, PAPP5-OX1 and PAPP5-OX2.

b) Examination of Photoresponsiveness

Seeds of the knock-out mutants and overexpression plants were surface-sterilized with 30% bleach (1.2% sodium hypochlorite) and 0.015% Triton X-100 for 10 minutes. Then, the seeds were washed five times with sterile water. For vernalization, the seeds were exposed to dark/cold-treatment for 3 days, and then placed on 0.8% phytoagar containing growth medium (0.1× Murashige-Skoog without sucrose; 0.1×MS). Then, the plate was exposed to continuous white light with an intensity of 200 $\mu molm^{-2}sec^{-1}$ (F48T12/CW/VHO, Philips) for 12 hours, and then incubated in dark conditions at 22° C. for 12 hours to promote germination. Before measuring the length of hypocotyl, the plate was placed under the various conditions (dark conditions, continuous red light (Rc) irradiation and continuous far-red-light (FRc) irradiation) for 4 days. Here, the light source was used as described in Kim, B. C. et al. *Plant J,* 9:441-456, 1996, and the fluence rate was monitored using a spectroradiometer (Hanbead Optical Power Meter 840, Newport). The length of hypocotyl was measured using a HP ScanJet 5370C digital scanner (Hewlett Packard) and Scion image software (Beta 4.0.2, Scion Corporation). Also, wild-type *Arabidopsis thaliana* (Col-0) and phytochrome mutants (phyB-9 and phyA-211) (distributed from *Arabidopsis* Biological Resource Center) were used as control plants.

FIG. 9 shows the curves of inhibition of hypocotyl length in the knock-out mutant (papp5-1) and the PAPP5-overexpressing plant (PAPP5 OX-2) according to Rc and FRc fluence rates, compared to those in the wild-type plant (Col-0) and the phytochrome mutant (phyB-9), in order to examine the photoresponsiveness of the plants. As shown in FIG. 9, the knock-out mutant papp5-1 showed the hyposensitivity to Rc and FRc of at lower fluence rate, whereas the PAPP5-overexpressing plants showed the hypersensitivity to Rc and FRc. Also, in the PAPP5-overexpressing plants, an "End-Of-Day Far-Red" (EOD-FR) response which is a phytochrome B-mediated response, and anthocyanin accumulation which is a phytochrome A-mediated response, were stronger than those in the wild-type plant (data not shown). It was found that the intensities of such light-dependent phenotypes were correlated with the PAPP5 transcript level.

Meanwhile, the knock-out mutant induced by the disruption of the PAPP5 gene showed long hypocotyls phenotype, diminished rates of light-induced hook opening and cotyledon separation, reduced cotyledon extension, and early flowering (data not shown). This suggests that PAPP5 is functionally involved in the photomorphogensis of plants, which is regulated by phytochromes.

Example 8

Analysis of Transcript Levels of Photoresponsive Genes in Knock-Out Mutants and Overexpression Plants To determine whether the involvement of PAPP5 in phytochrome-mediated light signal transduction be observed at a gene expression level, the expression levels of the following three genes whose expressions have been known to be regulated by light were examined in the knock-out mutants and the overexpression plants, compared to those in the wild-type plant: positively regulated genes, RBCS (GenBank accession No. X15221), CAB2 (GenBank accession No. X14564), and CHS (GenBank accession No. BT000596).

The seeds of each of the plants were placed individually onto 0.8% phytoagar plate containing 0.1×MS salts, and the plate was kept at 4° C. in dark condition for 3 days. In order to induce germination, the plate was exposed to white light with an intensity of 200 $\mu molm^{-2}sec^{-1}$ for 24 hours. Next, the seedlings were grown in dark conditions for further 4 days, and then, subsequently transferred to the following light conditions:

Rc: exposure at a wavelength of 664 nm and a quantity of light of 20 $\mu molm^{-2}sec^{-1}$ for 2 hours; and FRc: exposure at a wavelength of 748 nm and a quantity of light of 10 $\mu molm^{-2}sec^{-1}$ for 2 hours.

After tissue was harvested in green safe light, total RNA was isolated using the RNeasy plant mini kits (Qiagen) from the tissue. Then, 5 µg of the total RNA was separated on 1% agarose gel containing formaldehyde, and the gel was transferred to a nylon membrane. The membrane was hybridized with $^{32}$P-labeled probes specific to the each gene. Signals were quantified by a Fuji FLA-2000R image analyzer (Fuji Photo Film).

As a result, as shown in FIG. 10, upon dark treatment, RBCS, CAB2 and CHS mRNA were detected at low levels in all the plants. However, in the wild-type plants (Col-0, and Ws-2), the expression levels of the three genes were increased to high levels upon Rc and FRc irradiation. This coincides with the fact that phytochrome A and phytochrome B are involved in the regulation of these genes (Nagy, F. & Schafer, E. *Annu. Rev. Plant Biol.,* 53:329-355, 2002). Meanwhile, upon Rc and FRc irradiation, the PAPP5-overexpressing plant showed an increase in the expression levels of the genes as compared to the wild-type plant. On the other hand, in the knock-out mutants (papp5-1, and papp5-2), the expression levels of the genes were increased as compared to the case of dark treatment, but lower than that of the wild-type plant. This indicates those the photosensitivities of the RBCS, CAB2 and CHS genes in the knock-out mutants are lower than those in the wild-type plant. From the above results, it could be found that, due to the PAPP5 null mutation, the ability of phytochromes to transduce signals to the photosensitive genes was reduced.

Example 9

Dephosphorylation of Autophosphorylated Phytochrome by PAPP5

It was previously shown, using biochemical analyses, that reversible phosphorylation/de phosphorylation may be involved in the signal transduction and/or regulation of phytochrome activity (Yeh, K. C. & Lagarias, J. C. *Proc. Natl. Acad. Sci. U.S.A.* 95:13976-13981, 1998; Fankhauser, C. et al., *Science,* 284:1539-1541, 1999). Thus, in order to examine the molecular nature of PAPP5 interacting with phytochromes, the present inventors tested whether autophosphorylated phytochrome A can be directly dephosphorylated by PAPP5 in vitro.

First, KP buffer (20 mM Tris-HCl pH7.5, 30 mM $MgCl_2$, 1 mM EDTA, 1 mM EGTA, 0.1% β-mercaptoethanol, 0.1% ethanol) containing 1 μg of purified oat phytochrome A (provided from Kumho Life and Environmental Science Laboratory, Korea) was set on ice and irradiated with Rc light output of 50 $\mu molS^{-1}m^{-2}$ at 664 nm for 5 minutes. Then, the reaction solution was allowed to react with $[\gamma-^{32}P]$ATP in dark conditions for 30 minutes (autophosphorylation of phytochrome A). Following addition of 1 μg of each of the fusion proteins GST-PAPP5, GST-TPR and GST-PP2Ac prepared in Examples <4-1> and <5-1>, the reaction continued for more 30 minutes, and then stopped by adding 12 μl of 5× Tris-glycine SDS sample buffer under dim green safe light. The resulting reaction product was subjected to 10% SDS-PAGE, followed by autoradiography analysis with Fuji FLA-2000R image analyzer (Fuji Photo Film).

As a result, as shown in FIG. 11A, only GST-PAPP5 dephosphorylated the autophosphorylated oat Pfr phytochrome A by about 80%. Although the dephosphorylation of oat phytochrome A was also detectable in the reaction mixture containing the GST-PP2Ac, the level of dephosphorylation was very low. This suggests that PAPP5 dephosphorylates the autophosphylated Pfr-phytochrome as a main target, and thereby modulating the phosphorylation status of the Pfr-phytochrome. Namely, these results indicate that the autophosphorylated Pfr phytochrome A induces the phosphatase activity of PAPP5, and the activated PAPP5 directly dephosphorylates the autophosphorylated Pfr-phytochrome A. Also, these results indicate that simple physical association of TPR domain (GST-TPR) of PAPP5 or non-interactive catalytic domain of PAPP5 (GST-PP2Ac) do not affect the phosphorylation status of the Pfr-phytochrome.

Next, the present inventors investigated whether the phosphatase activity of PAPP5 depends on a change in the spectroscopic structure (photoconversion) of phytochrome molecules (Pr⇌Pfr). KP buffer solution containing phytochrome was set on ice and irradiated with a Rc light output of 50 $\mu molS^{-1}m^{-2}$ at 664 nm (conversion of phytochrome into Pfr form) or a FRc light output of 50 $\mu molS^{-1}m^{-2}$ at 748 nm (conversion of phytochrome into Pfr form) for 5 minutes. Then, the autophosphylation/dephosphorylation test of phytochrome was performed in the same manner as described above.

As a result, as shown in FIG. 11B, the dephosphorylation by PAPP5 was higher in Pfr phytochrome than that in Pf phytochrome.

The above results suggest that the phosphatase activity of PAPP5 for phytochrome is photoregulated, occurring predominantly in the phosphorylated Pfr-form. This correlation between the formation of the phytochrome-PAPP5 complex and the activation/stimulation of phosphatase activity suggests that PAPP5 specifically targets the phosphorylated Pfr-form of phytochrome by feedback manner.

Example 11

Production of Plants Overexpressing TPR Domain of PAPP5

A reverse genetic approach for dominant negative mutation was used to investigate the roles of TPR domain of PAPP5. The TPR domain-coding region (the sequence of amino acids 1-138 of SEQ ID NO: 4) was amplified by PCR using primers set forth in SEQ ID NO: 5 and SEQ ID NO: 10. The PCR reaction consisted of predenaturation of template DNA for 5 mm at 94° C., and then, 30 cycles of 30 sec at 94° C., 30 sec at 50° C. and 1 mm at 72° C., followed by 10 mm at 72° C. Thereafter, the PCR product was cloned into a pNB96 vector (see FIG. 12A). The prepared vector was named "pNB96-TPR". The pNB96-TPR vector was introduced into *Agrobacterium* strain AGL1 by electroporation. Next, according to the floral-dip method (SIGnAL T-DNA Express, Salk Institute Genomic Analysis Laboratory), *Arabidopsis thaliana* was transformed with the transformed *Agrobacterium*. 25 μg/μl of DL-PPT (Duchefa Biochemie BV) was used to select transgenic plants. Total 25 T1 lines were obtained and named "PAPP5-DN". Thereafter, on the basis of segregation of DL-PPT resistance, homozygous T3 seeds were isolated. The T3 plants were grown in the white light condition, and the resulting plants have shorter height, multiple shoots, and dwarfing of the floral shoot internodes, as compared to wild-type plants (see FIG. 12B). This is thought to be induced by improved protein-protein interaction, in view of the fact that the TPR domain of PAPP5 is involved in protein-protein interaction. Furthermore, this indicates that the introduction and overexpression of the TPR domain of PAPP5 in plants can introduce dwarf characteristics into the plants.

INDUSTRIAL APPLICABILITY

As described above, it was found a novel protein involved in light signal transduction regulating the growth and development of plants and its functions in the present invention. The inventive PAPP5 protein interconnects with phytochromes A and B. The PAPP5 protein contains a TPR domain involved in interaction with phytochromes, and a PP2A catalytic domain having phosphatase activity. The PAPP5 protein can be used as phosphatase. It is also useful in the production of plants sensitive to light signal transduction. Furthermore, the TPR domain present in the PAPP5 protein is useful in the production of dwarf plants.

What is claimed is:

1. A method for producing a dwarf plant, comprising the steps of:
   (a) inserting a polynucleotide encoding the sequence of amino acids 1-138 of SEQ ID NO: 4 into an expression vector; and
   (b) introducing the expression vector into a plant.

2. The method of claim 1, wherein the plant exhibits at least one phenotypic trait selected from the group consisting of shorter height, multiple shoots and dwarfing of floral shoot internodes, as compared to a wild-type plant.

3. A transgenic plant produced by the method of claim 1.

4. A plant tissue or seed derived from the transgenic plant of claim 3, wherein the plant tissue or seed comprises a polynucleotide encoding the sequence of amino acids 1-138 of SEQ ID NO: 4.

5. The plant of claim 3, wherein the plant is a dicotyledonous plant or a monocotyledonous plant.

* * * * *

SEQUENCE LISTING

```
<160> NUMBER OF SEQ ID NOS: 26

<210> SEQ ID NO 1
<211> LENGTH: 29
<212> TYPE: DNA
<213> ORGANISM: Artificial Sequence
<220> FEATURE:
```

<223> OTHER INFORMATION: PCR primer

<400> SEQUENCE: 1
ggatccaaat gtcaggctct aggccgact                                      29

<210> SEQ ID NO 2
<211> LENGTH: 30
<212> TYPE: DNA
<213> ORGANISM: Artificial Sequence
<220> FEATURE:
<223> OTHER INFORMATION: PCR primer

<400> SEQUENCE: 2
ctcgagctac ttgtttgctg cagcgagttc                                     30

<210> SEQ ID NO 3
<211> LENGTH: 1455
<212> TYPE: DNA
<213> ORGANISM: Arabidopsis thaliana

<400> SEQUENCE: 3

| | | | | | |
|---|---|---|---|---|---|
| atggagacca | agaatgagaa | ttctgatgtt | tcacgggcag | aggagtttaa | aagtcaggcc | 60 |
| aacgaagctt | ttaaaggtca | caaatactcc | agtgctattg | atctatatac | aaaagctatt | 120 |
| gaactcaaca | gcaacaacgc | tgtgtattgg | gcaaatcgtg | catttgctca | cacaaaactg | 180 |
| gaggaatatg | gcagtgcaat | acaggatgca | tcgaaggcca | ttgaagttga | ttcaagatac | 240 |
| tctaagggct | attacaggcg | tggtgctgcg | tatcttgcca | tgggaaaatt | taaggatgcc | 300 |
| ttgaaggact | tccaacaggt | aaaaaggctt | tctcctaatg | accctgatgc | cacaagaaag | 360 |
| ctaaaggaat | gtgagaaagc | agtgatgaaa | ctcaaatttg | aagaagcaat | ctctgtgcca | 420 |
| gtatctgaaa | ggcgttcagt | agctgagtcc | attgacttcc | atacaataga | ggttgagcca | 480 |
| caatattctg | gtgctagaat | tgagggagag | gaagttacct | tagattttgt | gaaaacgatg | 540 |
| atggaggatt | ttaagaacca | aaaaacattg | cataaacggt | atgcctatca | aatcgtctta | 600 |
| cagactaggc | aaatcttgct | agcactgcct | tctcttgttg | atataagtgt | tccacatggc | 660 |
| aaacatatca | ctgtttgcgg | tgacgttcat | ggtcagttct | acgatcttct | caatatcttt | 720 |
| gagcttaatg | cctccccttc | ggaggagaac | ccataccrat | ttaatggcga | ctttgtggac | 780 |
| agaggctcat | tctccgttga | gatcatcctc | actttgtttg | ctttcaagtg | catgtgccca | 840 |
| tcatccatat | atctagccag | aggaaaccat | gaaagcaaga | gcatgaacaa | aatttatggt | 900 |
| tttgagggtg | aggttcggtc | caagttgagt | gaaaaattcg | tggatctctt | tgctgaagtt | 960 |
| ttctgttacc | tcccgttggc | tcatgttata | aatgggaagg | tcttcgtggt | acatggaggt | 1020 |
| cttttcagtg | ttgacggcgt | gaaactctca | gacatcagag | ccattgacag | attctgtgag | 1080 |
| ccaccagagg | aaggactaat | gtgtgaacta | ttgtggagtg | atcctcaacc | tctccctgga | 1140 |
| agaggcccaa | gcaagcgagg | agttggtcta | tcatttggtg | gagatgtgac | aaagaggttt | 1200 |
| ttgcaagata | caaatttaga | tttgttggtc | cggtcacatg | aagtaaaaga | tgaaggttat | 1260 |
| gaggttgaac | atgacggtaa | actcataact | gtcttctctg | cgccaaatta | ctgtgatcag | 1320 |
| atgggtaata | agggagcctt | cattcgtttt | gaagctcctg | atatgaagcc | aaacattgtt | 1380 |
| acattctcag | cagtgcctca | tccggatgtg | aagcctatgg | catatgcaaa | caactttctc | 1440 |
| aggatgttca | actaa | | | | | 1455 |

<210> SEQ ID NO 4
<211> LENGTH: 484

```
<212> TYPE: PRT
<213> ORGANISM: Arabidopsis thaliana

<400> SEQUENCE: 4

Met Glu Thr Lys Asn Glu Asn Ser Asp Val Ser Arg Ala Glu Phe
 1               5                  10                  15

Lys Ser Gln Ala Asn Glu Ala Phe Lys Gly His Lys Tyr Ser Ser Ala
             20                  25                  30

Ile Asp Leu Tyr Thr Lys Ala Ile Glu Leu Asn Ser Asn Asn Ala Val
             35                  40                  45

Tyr Trp Ala Asn Arg Ala Phe Ala His Thr Lys Leu Glu Glu Tyr Gly
 50                  55                  60

Ser Ala Ile Gln Asp Ala Ser Lys Ala Ile Glu Val Asp Ser Arg Tyr
 65                  70                  75                  80

Ser Lys Gly Tyr Tyr Arg Arg Gly Ala Ala Tyr Leu Ala Met Gly Lys
                 85                  90                  95

Phe Lys Asp Ala Leu Lys Asp Phe Gln Gln Val Lys Arg Leu Ser Pro
            100                 105                 110

Asn Asp Pro Asp Ala Thr Arg Lys Leu Lys Glu Cys Glu Lys Ala Val
            115                 120                 125

Met Lys Leu Lys Phe Glu Glu Ala Ile Ser Val Pro Val Ser Glu Arg
            130                 135                 140

Arg Ser Val Ala Glu Ser Ile Asp Phe His Thr Ile Glu Val Glu Pro
145                 150                 155                 160

Gln Tyr Ser Gly Ala Arg Ile Glu Gly Glu Val Thr Leu Asp Phe
                165                 170                 175

Val Lys Thr Met Met Glu Asp Phe Lys Asn Gln Lys Thr Leu His Lys
            180                 185                 190

Arg Tyr Ala Tyr Gln Ile Val Leu Gln Thr Arg Gln Ile Leu Leu Ala
            195                 200                 205

Leu Pro Ser Leu Val Asp Ile Ser Val Pro His Gly Lys His Ile Thr
            210                 215                 220

Val Cys Gly Asp Val His Gly Gln Phe Tyr Asp Leu Leu Asn Ile Phe
225                 230                 235                 240

Glu Leu Asn Gly Leu Pro Ser Glu Glu Asn Pro Tyr Leu Phe Asn Gly
                245                 250                 255

Asp Phe Val Asp Arg Gly Ser Phe Ser Val Glu Ile Ile Leu Thr Leu
            260                 265                 270

Phe Ala Phe Lys Cys Met Cys Pro Ser Ile Tyr Leu Ala Arg Gly
            275                 280                 285

Asn His Glu Ser Lys Ser Met Asn Lys Ile Tyr Gly Phe Glu Gly Glu
            290                 295                 300

Val Arg Ser Lys Leu Ser Glu Lys Phe Val Asp Leu Phe Ala Glu Val
305                 310                 315                 320

Phe Cys Tyr Leu Pro Leu Ala His Val Ile Asn Gly Lys Val Phe Val
                325                 330                 335

Val His Gly Gly Leu Phe Ser Val Asp Gly Val Lys Leu Ser Asp Ile
            340                 345                 350

Arg Ala Ile Asp Arg Phe Cys Glu Pro Pro Glu Glu Gly Leu Met Cys
            355                 360                 365

Glu Leu Leu Trp Ser Asp Pro Gln Pro Leu Pro Gly Arg Gly Pro Ser
            370                 375                 380

Lys Arg Gly Val Gly Leu Ser Phe Gly Gly Asp Val Thr Lys Arg Phe
385                 390                 395                 400
```

```
Leu Gln Asp Asn Asn Leu Asp Leu Leu Val Arg Ser His Glu Val Lys
                405                 410                 415
Asp Glu Gly Tyr Glu Val Glu His Asp Gly Lys Leu Ile Thr Val Phe
            420                 425                 430
Ser Ala Pro Asn Tyr Cys Asp Gln Met Gly Asn Lys Gly Ala Phe Ile
        435                 440                 445
Arg Phe Glu Ala Pro Asp Met Lys Pro Asn Ile Val Thr Phe Ser Ala
    450                 455                 460
Val Pro His Pro Asp Val Lys Pro Met Ala Tyr Ala Asn Asn Phe Leu
465                 470                 475                 480
Arg Met Phe Asn

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
ggatccatgg agaccaagaa tgag                                          24

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
ctcgagttag ttgaacatcc tgag                                          24

<210> SEQ ID NO 7
<211> LENGTH: 28
<212> TYPE: DNA
<213> ORGANISM: Artificial Sequence
<220> FEATURE:
<223> OTHER INFORMATION: PCR primer

<400> SEQUENCE: 7
ggatccgatg tcaggctcta ggccgact                                      28

<210> SEQ ID NO 8
<211> LENGTH: 34
<212> TYPE: DNA
<213> ORGANISM: Artificial Sequence
<220> FEATURE:
<223> OTHER INFORMATION: PCR primer

<400> SEQUENCE: 8
gctgatcagc atggtttccg gagtcggggg tagt                               34

<210> SEQ ID NO 9
<211> LENGTH: 34
<212> TYPE: DNA
<213> ORGANISM: Artificial Sequence
<220> FEATURE:
<223> OTHER INFORMATION: PCR primer

<400> SEQUENCE: 9
cccggccgga ctaatatggc atcatcagca tcat                               34
```

<210> SEQ ID NO 10
<211> LENGTH: 27
<212> TYPE: DNA
<213> ORGANISM: Artificial Sequence
<220> FEATURE:
<223> OTHER INFORMATION: PCR primer

<400> SEQUENCE: 10
ctcgagtcaa gagattgctt cttcaaa         27

<210> SEQ ID NO 11
<211> LENGTH: 27
<212> TYPE: DNA
<213> ORGANISM: Artificial Sequence
<220> FEATURE:
<223> OTHER INFORMATION: PCR primer

<400> SEQUENCE: 11
ggatccatgc cagtatctga aaggcgt         27

<210> SEQ ID NO 12
<211> LENGTH: 24
<212> TYPE: DNA
<213> ORGANISM: Artificial Sequence
<220> FEATURE:
<223> OTHER INFORMATION: PCR primer

<400> SEQUENCE: 12
atggagacca agaatgagaa ttct             24

<210> SEQ ID NO 13
<211> LENGTH: 24
<212> TYPE: DNA
<213> ORGANISM: Artificial Sequence
<220> FEATURE:
<223> OTHER INFORMATION: PCR primer

<400> SEQUENCE: 13
ttagttgaac atcctgagaa agtt             24

<210> SEQ ID NO 14
<211> LENGTH: 347
<212> TYPE: PRT
<213> ORGANISM: Arabidopsis thaliana

<400> SEQUENCE: 14

Ser Val Pro Val Ser Glu Arg Arg Ser Val Ala Glu Ser Ile Asp Phe
 1               5                  10                  15

His Thr Ile Glu Val Glu Pro Gln Tyr Ser Gly Ala Arg Ile Glu Gly
            20                  25                  30

Glu Glu Val Thr Leu Asp Phe Val Lys Thr Met Met Glu Asp Phe Lys
        35                  40                  45

Asn Gln Lys Thr Leu His Lys Arg Tyr Ala Tyr Gln Ile Val Leu Gln
    50                  55                  60

Thr Arg Gln Ile Leu Leu Ala Leu Pro Ser Leu Val Asp Ile Ser Val
65                  70                  75                  80

Pro His Gly Lys His Ile Thr Val Cys Gly Asp Val His Gly Gln Phe
                85                  90                  95

Tyr Asp Leu Leu Asn Ile Phe Glu Leu Asn Gly Leu Pro Ser Glu Glu
            100                 105                 110

Asn Pro Tyr Leu Phe Asn Gly Asp Phe Val Asp Arg Gly Ser Phe Ser
        115                 120                 125

```
Val Glu Ile Ile Leu Thr Leu Phe Ala Phe Lys Cys Met Cys Pro Ser
            130                 135                 140

Ser Ile Tyr Leu Ala Arg Gly Asn His Glu Ser Lys Ser Met Asn Lys
145                 150                 155                 160

Ile Tyr Gly Phe Glu Gly Glu Val Arg Ser Lys Leu Ser Glu Lys Phe
                165                 170                 175

Val Asp Leu Phe Ala Glu Val Phe Cys Tyr Leu Pro Leu Ala His Val
            180                 185                 190

Ile Asn Gly Lys Val Phe Val His Gly Gly Leu Phe Ser Val Asp
            195                 200                 205

Gly Val Lys Leu Ser Asp Ile Arg Ala Ile Asp Arg Phe Cys Glu Pro
    210                 215                 220

Pro Glu Glu Gly Leu Met Cys Glu Leu Leu Trp Ser Asp Pro Gln Pro
225                 230                 235                 240

Leu Pro Gly Arg Gly Pro Ser Lys Arg Gly Val Gly Leu Ser Phe Gly
                245                 250                 255

Gly Asp Val Thr Lys Arg Phe Leu Gln Asp Asn Asn Leu Asp Leu Leu
            260                 265                 270

Val Arg Ser His Glu Val Lys Asp Glu Gly Tyr Glu Val Glu His Asp
            275                 280                 285

Gly Lys Leu Ile Thr Val Phe Ser Ala Pro Asn Tyr Cys Asp Gln Met
    290                 295                 300

Gly Asn Lys Gly Ala Phe Ile Arg Phe Glu Ala Pro Asp Met Lys Pro
305                 310                 315                 320

Asn Ile Val Thr Phe Ser Ala Val Pro His Pro Asp Val Lys Pro Met
                325                 330                 335

Ala Tyr Ala Asn Asn Phe Leu Arg Met Phe Asn
            340                 345

<210> SEQ ID NO 15
<211> LENGTH: 1041
<212> TYPE: DNA
<213> ORGANISM: Arabidopsis thaliana

<400> SEQUENCE: 15
gtgccagtat ctgaaaggcg ttcagtagct gagtccattg acttccatac aatagaggtt      60
gagccacaat attctggtgc tagaattgag ggagaggaag ttaccttaga ttttgtgaaa     120
acgatgatgg aggattttaa gaaccaaaaa acattgcata acggtatgc ctatcaaatc      180 gtcttacaga ctaggcaaat cttgctagca ctgccttctc ttgttgatat aagtgttcca     240
catggcaaac atatcactgt ttgcggtgac gttcatggtc agttctacga tcttctcaat     300
atctttgagc ttaatggcct cccttcggag gagaacccat acctatttaa tggcgacttt     360
gtggacagag gctcattctc cgttgagatc atcctcactt tgtttgcttt caagtgcatg     420
tgcccatcat ccatatatct agccagagga accatgaaa gcaagagcat gaacaaaatt     480
tatggttttg agggtgaggt tcggtccaag ttgagtgaaa aattcgtgga tctctttgct     540
gaagttttct gttacctccc gttggctcat gttataaatg ggaaggtctt cgtggtacat     600
ggaggtcttt tcagtgttga cggcgtgaaa ctctcagaca tcagagccat tgacagattc     660
tgtgagccac cagaggaagg actaatgtgt gaactattgt ggagtgatcc tcaacctctc     720
cctggaagag gcccaagcaa gcgaggagtt ggtctatcat ttggtggaga tgtgacaaag     780 aggttttgc aagataacaa tttagatttg ttggtccggt cacatgaagt aaaagatgaa     840
ggttatgagg ttgaacatga cggtaaactc ataactgtct ctctgcgcc aaattactgt     900
```

-continued

```
gatcagatgg gtaataaggg agccttcatt cgttttgaag ctcctgatat gaagccaaac    960
attgttacat tctcagcagt gcctcatccg gatgtgaagc ctatggcata tgcaaacaac   1020
tttctcagga tgttcaacta a                                             1041
```

<210> SEQ ID NO 16
<211> LENGTH: 479
<212> TYPE: PRT
<213> ORGANISM: Homo sapiens
<220> FEATURE:
<221> NAME/KEY: PEPTIDE
<222> LOCATION: (1)
<223> OTHER INFORMATION: PAPP5

<400> SEQUENCE: 16

```
Met Glu Thr Lys Asn Glu Asn Ser Asp Val Ser Arg Ala Glu Glu Phe
 1               5                  10                  15

Lys Ser Gln Ala Asn Glu Ala Phe Lys Gly His Lys Tyr Ser Ser Ala
            20                  25                  30

Ile Asp Leu Tyr Thr Lys Ala Ile Glu Leu Asn Ser Asn Asn Ala Val
        35                  40                  45

Tyr Trp Ala Asn Arg Ala Phe Ala His Thr Lys Leu Glu Glu Tyr Gly
    50                  55                  60

Ser Ala Ile Gln Asp Ala Ser Lys Ala Ile Glu Val Asp Ser Arg Tyr
65                  70                  75                  80

Ser Lys Gly Tyr Tyr Arg Arg Gly Ala Ala Tyr Leu Ala Met Gly Lys
                85                  90                  95

Glu Lys Asp Ala Leu Lys Asp Phe Gln Gln Val Lys Gly Leu Ser Pro
            100                 105                 110

Asn Asp Pro Asp Ala Thr Arg Lys Leu Lys Glu Cys Glu Lys Ala Val
        115                 120                 125

Met Lys Leu Lys Phe Glu Glu Ala Ile Ser Val Pro Val Ser Glu Arg
    130                 135                 140

Arg Ser Val Ala Glu Ser Ile Asp Phe His Thr Ile Glu Val Glu Pro
145                 150                 155                 160

Gln Tyr Ser Gly Ala Arg Ile Glu Gly Glu Val Thr Leu Asp Phe
                165                 170                 175

Val Lys Thr Met Met Glu Asp Phe Lys Asn Gln Lys Thr Leu His Lys
            180                 185                 190

Arg Tyr Ala Tyr Gln Ile Val Leu Gln Thr Arg Gln Ile Leu Leu Ala
        195                 200                 205

Leu Pro Ser Leu Val Asp Ile Ser Val Pro His Gly Lys His Ile Thr
    210                 215                 220

Val Cys Gly Asp Val His Gly Gln Phe Tyr Asp Leu Leu Asn Ile Phe
225                 230                 235                 240

Glu Asp Asn Gly Leu Pro Ser Glu Glu Asn Pro Tyr Leu Phe Asn Gly
                245                 250                 255

Asp Phe Val Asp Arg Gly Ser Phe Ser Val Glu Ile Ile Leu Thr Leu
            260                 265                 270

Phe Ala Glu Lys Cys Met Cys Pro Ser Ser Ile Tyr Leu Ala Arg Gly
        275                 280                 285

Asn His Glu Ser Lys Ser Met Asn Lys Ile Tyr Gly Phe Glu Gly Glu
    290                 295                 300

Val Arg Ser Lys Leu Ser Glu Lys Phe Val Asp Leu Phe Ala Glu Val
305                 310                 315                 320
```

-continued

```
Phe Cys Tyr Leu Pro Leu Ala His Val Ile Asn Gly Lys Val Phe Val
            325                 330                 335

Val His Gly Gly Leu Phe Ser Val Asp Gly Val Lys Leu Ser Asp Ile
        340                 345                 350

Arg Ala Ile Asp Arg Phe Cys Glu Pro Phe Glu Gly Leu Met Cys
            355                 360                 365

Glu Leu Leu Trp Ser Asp Pro Gln Pro Leu Pro Gly Arg Gly Pro Ser
    370                 375                 380

Lys Arg Gly Val Gly Leu Ser Phe Gly Gly Asp Val Thr Lys Arg Phe
385                 390                 395                 400

Leu Gln Asp Asn Asn Leu Asp Leu Leu Val Arg Ser His Glu Val Lys
                405                 410                 415

Asp Glu Gly Tyr Glu Val Glu His Asp Gly Lys Leu Ile Thr Val Phe
            420                 425                 430

Ser Ala Pro Asn Cys Asp Gln Met Gly Asn Lys Gly Ala Phe Ile Arg
        435                 440                 445

Phe Glu Ala Pro Asp Met Lys Pro Asn Ile Val Thr Phe Ser Ala Val
    450                 455                 460

Pro His Pro Met Ala Tyr Ala Asn Asn Phe Ile Arg Met Phe Asn
465                 470                 475

<210> SEQ ID NO 17
<211> LENGTH: 492
<212> TYPE: PRT
<213> ORGANISM: Homo sapiens
<220> FEATURE:
<221> NAME/KEY: PEPTIDE
<222> LOCATION: (1)
<223> OTHER INFORMATION: PP5

<400> SEQUENCE: 17

Glu Arg Thr Glu Cys Ala Glu Pro Pro Arg Asp Glu Pro Pro Ala Asp
1               5                   10                  15

Gly Ala Leu Lys Arg Ala Glu Glu Leu Lys Thr Gln Ala Asn Asp Tyr
            20                  25                  30

Phe Lys Ala Lys Asp Tyr Glu Asn Ala Ile Lys Phe Tyr Ser Gln Ala
        35                  40                  45

Ile Glu Leu Asn Pro Ser Asn Ala Ile Tyr Tyr Gly Asn Arg Ser Leu
    50                  55                  60

Ala Tyr Leu Arg Thr Glu Cys Tyr Gly Tyr Ala Leu Gly Asp Ala Thr
65                  70                  75                  80

Arg Ala Ile Glu Leu Asp Lys Lys Tyr Ile Lys Gly Tyr Tyr Arg Arg
            85                  90                  95

Ala Ala Ser Asn Met Ala Leu Gly Lys Phe Arg Ala Ala Leu Arg Asp
        100                 105                 110

Tyr Glu Thr Val Val Lys Val Lys Pro His Asp Lys Asp Ala Lys Met
    115                 120                 125

Lys Tyr Gln Glu Cys Asn Lys Thr Val Lys Gln Lys Ala Phe Glu Arg
130                 135                 140

Ala Ile Gly Asp Glu His Lys Arg Ser Val Val Asp Ser Leu Asp Ile
145                 150                 155                 160

Glu Ser Met Thr Ile Glu Asp Glu Tyr Ser Gly Pro Lys Leu Glu Asp
            165                 170                 175

Gly Lys Val Thr Ile Ser Phe Met Lys Glu Leu Met Gln Trp Tyr Lys
        180                 185                 190

Asp Gln Lys Lys Leu His Arg Lys Cys Ala Tyr Gln Ile Leu Val Gln
```

```
                195                 200                 205
Val Lys Glu Val Leu Ser Lys Leu Ser Thr Leu Val Glu Thr Thr Leu
    210                 215                 220

Lys Glu Thr Glu Lys Ile Thr Val Cys Gly Asp Thr His Gly Gln Phe
225                 230                 235                 240

Tyr Asp Leu Leu Asn Ile Phe Glu Leu Asn Gly Leu Pro Ser Glu Thr
                245                 250                 255

Asn Pro Tyr Asp Phe Asn Gly Asp Phe Val Asp Arg Gly Ser Phe Ser
            260                 265                 270

Val Glu Val Ile Leu Thr Leu Phe Gly Phe Lys Leu Leu Tyr Pro Asp
        275                 280                 285

His Phe His Leu Leu Arg Gly Asn His Glu Thr Asp Asn Met Asn Gln
    290                 295                 300

Ile Tyr Gly Phe Glu Gly Glu Val Lys Ala Lys Tyr Thr Ala Gln Met
305                 310                 315                 320

Tyr Glu Leu Phe Ser Glu Val Phe Glu Trp Leu Pro Leu Ala Gln Cys
                325                 330                 335

Ile Asn Gly Lys Val Leu Ile Met His Gly Gly Leu Phe Ser Glu Asp
            340                 345                 350

Gly Val Thr Leu Asp Asp Ile Arg Lys Ile Glu Arg Asn Arg Gln Pro
        355                 360                 365

Phe Asp Ser Gly Pro Met Cys Asp Leu Leu Trp Ser Asp Pro Gln Pro
    370                 375                 380

Gln Asn Gly Arg Ser Ile Ser Lys Arg Gly Val Ser Cys Gln Phe Gly
385                 390                 395                 400

Pro Asp Val Thr Lys Ala Phe Leu Glu Glu Asn Asn Leu Asp Tyr Ile
                405                 410                 415

Ile Arg Ser His Glu Val Lys Ala Glu Gly Tyr Glu Val Ala His Gly
            420                 425                 430

Gly Arg Cys Val Thr Val Phe Ser Ala Pro Asn Tyr Cys Asp Gln Met
        435                 440                 445

Gly Asn Lys Ala Ser Tyr Ile His Leu Gln Gly Ser Asp Leu Arg Pro
    450                 455                 460

Gln Phe His Gln Phe Thr Ala Val Pro His Pro Asn Val Lys Pro Met
465                 470                 475                 480

Ala Tyr Ala Asn Thr Leu Leu Gln Leu Gly Met Met
                485                 490

<210> SEQ ID NO 18
<211> LENGTH: 500
<212> TYPE: PRT
<213> ORGANISM: Mus musculus
<220> FEATURE:
<221> NAME/KEY: PEPTIDE
<222> LOCATION: (1)
<223> OTHER INFORMATION: PP5

<400> SEQUENCE: 18

Met Ala Met Ala Glu Gly Glu Arg Thr Glu Cys Ala Glu Thr Pro Arg
  1               5                  10                  15

Asp Glu Pro Pro Ala Asp Gly Leu Ala Lys Arg Ala Glu Glu Leu Lys
                20                  25                  30

Thr Gln Ala Asn Asp Tyr Phe Lys Ala Lys Asp Tyr Glu Asn Ala Ile
            35                  40                  45

Lys Phe Tyr Ser Gln Ala Ile Glu Leu Asn Pro Gly Asn Ala Ile Tyr
        50                  55                  60
```

```
Tyr Gly Asn Arg Ser Leu Ala Tyr Leu Arg Thr Glu Cys Tyr Gly Tyr
 65                  70                  75                  80

Ala Leu Gly Asp Ala Thr Arg Ala Ile Glu Leu Asp Lys Lys Tyr Ile
                 85                  90                  95

Lys Gly Tyr Tyr Arg Arg Ala Ala Ser Asn Met Ala Leu Gly Lys Phe
            100                 105                 110

Arg Ala Ala Leu Arg Asp Tyr Glu Thr Val Val Lys Val Lys Pro Asn
        115                 120                 125

Asp Lys Asp Ala Lys Met Lys Tyr Gln Glu Cys Ser Lys Thr Val Lys
    130                 135                 140

Gln Lys Ala Phe Glu Arg Ala Ile Ala Gly Asp Glu His Arg Arg Ser
145                 150                 155                 160

Val Val Asp Ser Leu Asp Ile Glu Ser Met Thr Ile Glu Asp Glu Tyr
                165                 170                 175

Ser Gly Pro Lys Leu Glu Asp Gly Lys Val Thr Ile Thr Phe Met Lys
            180                 185                 190

Asp Leu Met Gln Trp Tyr Lys Asp Gln Lys Lys Leu His Arg Lys Cys
        195                 200                 205

Ala Tyr Gln Ile Leu Val Gln Val Lys Glu Val Leu Cys Lys Leu Ser
    210                 215                 220

Thr Leu Val Glu Thr Thr Leu Lys Glu Thr Glu Lys Ile Thr Val Cys
225                 230                 235                 240

Gly Asp Thr His Gly Gln Phe Tyr Asp Leu Leu Asn Ile Phe Glu Leu
                245                 250                 255

Asn Gly Leu Pro Ser Glu Thr Thr Asn Pro Tyr Thr Phe Asn Gly Asp
            260                 265                 270

Phe Val Asp Arg Gly Ser Phe Ser Val Glu Val Ile Leu Thr Leu Phe
        275                 280                 285

Gly Phe Lys Leu Leu Tyr Pro Asp His Phe His Leu Leu Arg Gly Asn
    290                 295                 300

His Glu Thr Asp Asn Met Asn Gln Ile Tyr Gly Phe Glu Gly Glu Val
305                 310                 315                 320

Lys Ala Lys Tyr Thr Ala Gln Met Tyr Glu Leu Phe Ser Glu Val Glu
                325                 330                 335

Glu Trp Leu Pro Leu Ala Gln Cys Ile Asn Gly Lys Val Leu Ile Met
            340                 345                 350

His Gly Gly Leu Phe Ser Glu Asp Gly Val Thr Leu Asp Asp Ile Arg
        355                 360                 365

Lys Ile Glu Arg Asn Arg Gln Pro Pro Asp Ser Gly Pro Met Cys Asp
    370                 375                 380

Leu Leu Trp Ser Asp Pro Gln Pro Gln Asn Gly Arg Ser Val Ser Lys
385                 390                 395                 400

Arg Gly Val Ser Cys Gln Phe Gly Pro Asp Val Thr Lys Ala Phe Leu
                405                 410                 415

Glu Glu Asn Gln Leu Asp Tyr Ile Ile Arg Ser His Glu Val Lys Ala
            420                 425                 430

Glu Gly Tyr Glu Val Ala His Gly Gly Arg Cys Val Thr Val Phe Ser
        435                 440                 445

Ala Pro Asn Tyr Cys Asp Gln Met Gly Asn Lys Ala Ser Tyr Ile His
    450                 455                 460

Leu Gln Gly Ser Asp Leu Arg Pro Gln Phe His Gln Phe Thr Ala Val
465                 470                 475                 480
```

```
Pro His Pro Asn Val Lys Pro Met Ala Tyr Ala Asn Thr Leu Leu Gln
                485                 490                 495

Leu Gly Met Met
            500

<210> SEQ ID NO 19
<211> LENGTH: 497
<212> TYPE: PRT
<213> ORGANISM: Rattus norvegicus
<220> FEATURE:
<221> NAME/KEY: PEPTIDE
<222> LOCATION: (1)
<223> OTHER INFORMATION: PP5

<400> SEQUENCE: 19

Met Ala Met Ala Glu Gly Glu Arg Thr Glu Cys Ala Glu Pro Pro Arg
  1               5                  10                  15

Asp Pro Pro Ala Glu Gly Thr Leu Lys Arg Ala Glu Glu Leu Lys
             20                  25                  30

Thr Gln Ala Asn Asp Tyr Phe Lys Ala Lys Asp Tyr Glu Asn Ala Ile
         35                  40                  45

Lys Phe Tyr Ser Gln Ala Ile Glu Leu Asn Pro Ser Asn Ala Ile Tyr
 50                  55                  60

Tyr Gly Asn Arg Ser Leu Ala Tyr Leu Arg Thr Glu Cys Tyr Gly Tyr
 65                  70                  75                  80

Ala Leu Gly Asp Ala Thr Arg Ala Ile Glu Leu Asp Lys Lys Tyr Ile
                 85                  90                  95

Lys Gly Tyr Tyr Arg Arg Ala Ala Ser Asn Met Ala Leu Gly Lys Phe
            100                 105                 110

Arg Ala Ala Leu Arg Asp Tyr Glu Thr Val Val Lys Pro Asn Asp Lys
        115                 120                 125

Asp Ala Lys Met Lys Tyr Gln Glu Cys Ser Lys Thr Val Lys Gln Lys
    130                 135                 140

Gln Phe Glu Arg Ala Ile Ala Gly Asp Glu His Arg Arg Ser Val Val
145                 150                 155                 160

Asp Ser Leu Asp Ile Glu Ser Met Thr Leu Glu Asp Glu Tyr Ser Gly
                165                 170                 175

Pro Lys Leu Glu Asp Gly Lys Val Thr Ile Thr Phe Met Lys Asp Leu
            180                 185                 190

Met Gln Trp Tyr Lys Asp Gln Lys Lys Leu His Arg Lys Cys Ala Tyr
        195                 200                 205

Gln Ile Leu Val Gln Val Lys Glu Val Leu Val Lys Leu Ser Thr Leu
    210                 215                 220

Val Glu Thr Thr Leu Lys Glu Thr Glu Lys Ile Thr Val Cys Gly Asp
225                 230                 235                 240

Thr His Gly Gln Phe Tyr Asp Leu Leu Asn Glu Phe Glu Leu Asn Gly
                245                 250                 255

Leu Pro Ser Glu Thr Asn Pro Tyr Ile Glu Asn Gly Asp Phe Val Asp
            260                 265                 270

Arg Gly Ser Phe Ser Val Glu Val Ile Leu Thr Leu Phe Gly Phe Lys
        275                 280                 285

Leu Leu Tyr Pro Asp His Phe His Leu Leu Arg Gly Asn His Glu Thr
    290                 295                 300

Asp Asn Met Asn Gln Ile Tyr Gly Phe Glu Gly Glu Val Lys Ala Lys
305                 310                 315                 320

Tyr Thr Ala Gln Met Tyr Glu Leu Phe Ser Glu Val Glu Glu Trp Leu
```

-continued

```
               325                 330                 335
Pro Leu Ala Gln Cys Ile Asn Gly Lys Val Leu Ile Met His Gly Gly
            340                 345                 350

Leu Phe Ser Glu Asp Gly Val Thr Leu Asp Asp Ile Pro Lys Ile Glu
            355                 360                 365

Arg Asn Arg Gln Pro Phe Asp Ser Gly Pro Met Cys Asp Leu Leu Trp
        370                 375                 380

Ser Asp Pro Gln Pro Gln Asn Gly Arg Ser Val Ser Lys Arg Gly Val
385                 390                 395                 400

Ser Cys Gln Phe Gly Pro Asp Val Thr Lys Ala Phe Leu Glu Glu Asn
                405                 410                 415

Gln Leu Asp Tyr Ile Ile Arg Ser His Glu Val Lys Ala Glu Gly Tyr
            420                 425                 430

Glu Val Ala His Gly Gly Arg Cys Val Thr Val Phe Ser Ala Pro Asn
            435                 440                 445

Tyr Cys Asp Gln Met Gly Asn Lys Ala Ser Tyr Ile His Leu Gln Gly
        450                 455                 460

Ser Asp Leu Arg Pro Gln Phe His Gln Phe Thr Ala Val Pro His Pro
465                 470                 475                 480

Asn Val Lys Pro Met Ala Tyr Ala Asn Ile Leu Leu Gln Leu Gly Met
                485                 490                 495

Met
```

<210> SEQ ID NO 20
<211> LENGTH: 513
<212> TYPE: PRT
<213> ORGANISM: Saccharomyces cerevisiae
<220> FEATURE:
<221> NAME/KEY: PEPTIDE
<222> LOCATION: (1)
<223> OTHER INFORMATION: PP5

<400> SEQUENCE: 20

```
Met Ser Thr Pro Thr Ala Ala Asp Arg Ala Lys Ala Leu Glu Arg Lys
  1               5                  10                  15

Asn Glu Gly Asn Val Phe Val Lys Glu Lys His Phe Leu Lys Ala Ile
                 20                  25                  30

Glu Lys Tyr Thr Glu Ala Ile Asp Leu Asp Ser Thr Gln Ser Ile Tyr
             35                  40                  45

Phe Ser Asn Arg Ala Phe Ala His Phe Lys Val Asp Asn Phe Gln Ser
         50                  55                  60

Ala Leu Asn Asp Cys Asp Glu Ala Ile Lys Leu Asp Pro Lys Asn Ile
 65                  70                  75                  80

Lys Ala Tyr His Arg Arg Ala Leu Ser Cys Met Ala Leu Leu Glu Glu
                 85                  90                  95

Lys Lys Ala Arg Lys Asp Leu Asn Val Leu Leu Lys Ala Lys Pro Asn
                100                 105                 110

Asp Pro Ala Ala Thr Lys Ala Leu Leu Thr Cys Asp Arg Phe Ile Arg
            115                 120                 125

Glu Glu Arg Phe Arg Lys Ala Ile Gly Gly Ala Glu Asn Glu Ala Lys
        130                 135                 140

Ile Ser Leu Cys Gln Thr Leu Asn Leu Ser Ser Phe Asp Ala Asn Ala
145                 150                 155                 160

Asp Leu Ala Asn Tyr Glu Gly Pro Lys Leu Glu Phe Glu Gln Leu Tyr
                165                 170                 175
```

```
-continued

Asp Asp Lys Asn Ala Phe Lys Gly Ala Lys Ile Lys Asn Met Ser Gln
            180                 185                 190

Glu Phe Ile Ser Lys Met Val Asn Asp Leu Phe Leu Lys Gly Lys Tyr
            195                 200                 205

Leu Pro Lys Lys Tyr Val Ala Ala Ile Thr Ser His Ala Asp Thr Leu
    210                 215                 220

Phe Arg Gln Glu Pro Ser Met Val Glu Leu Glu Asn Asn Ser Thr Pro
225                 230                 235                 240

Asp Val Lys Ile Ser Val Cys Gly Asp Thr His Gly Gln Phe Tyr Asp
                245                 250                 255

Val Leu Asn Leu Phe Arg Lys Phe Gly Lys Val Gly Pro Lys His Thr
            260                 265                 270

Tyr Leu Phe Asn Gly Asp Phe Val Asp Arg Gly Ser Trp Ser Cys Glu
            275                 280                 285

Val Ala Leu Leu Phe Tyr Cys Leu Lys Ile Leu His Pro Asn Asn Phe
        290                 295                 300

Phe Leu Asn Arg Gly Asn His Glu Ser Asp Asn Met Asn Lys Ile Tyr
305                 310                 315                 320

Gly Phe Glu Asp Glu Cys Lys Tyr Lys Tyr Ser Gln Arg Thr Phe Asn
                325                 330                 335

Met Phe Ala Gln Ser Phe Glu Ser Leu Pro Leu Ala Thr Leu Ile Asn
            340                 345                 350

Asn Asp Tyr Leu Val Met His Gly Gly Leu Pro Ser Asp Pro Ser Ala
            355                 360                 365

Thr Leu Ser Asp Phe Lys Asn Ile Asp Arg Phe Ala Gln Pro Pro Arg
    370                 375                 380

Asp Gly Ala Phe Met Glu Leu Leu Trp Ala Asp Pro Gln Glu Ala Asn
385                 390                 395                 400

Gly Met Gly Pro Ser Gln Arg Gly Leu Gly His Ala Phe Gly Pro Asp
                405                 410                 415

Ile Thr Asp Arg Phe Leu Arg Asn Asn Lys Leu Arg Lys Ile Phe Arg
            420                 425                 430

Ser His Glu Leu Arg Met Gly Gly Val Gln Phe Glu Gln Lys Gly Lys
            435                 440                 445

Leu Met Thr Val Phe Ser Ala Pro Asn Tyr Cys Asp Ser Gln Gly Asn
    450                 455                 460

Leu Gly Gly Val Ile His Val Pro Gly His Gly Ile Leu Gln Ala
465                 470                 475                 480

Gly Arg Asn Asp Asp Gln Asn Leu Ile Ile Glu Thr Phe Glu Ala Val
                485                 490                 495

Glu His Pro Asp Ile Lys Pro Met Ala Tyr Ser Asn Gly Gly Phe Gly
                500                 505                 510

Leu

<210> SEQ ID NO 21
<211> LENGTH: 520
<212> TYPE: PRT
<213> ORGANISM: Drosophila melanogaster
<220> FEATURE:
<221> NAME/KEY: PEPTIDE
<222> LOCATION: (1)
<223> OTHER INFORMATION: PP5

<400> SEQUENCE: 21

Met Ser Ser Ser Glu Leu Glu Val Gln Lys Ala Ala Asp Cys Gln Gln
1               5                   10                  15
```

```
Glu Ala Lys Val Pro Ala Ser Val Glu Ile Thr Gly Ser Lys Gln Pro
             20                  25                  30

Glu Glu Asp Thr Asn Ala Arg Thr Lys Ala Glu Leu Asp Phe Ala Ala
         35                  40                  45

Ala Glu Gln Tyr Lys Asn Gln Gly Asn Glu Met Leu Lys Thr Lys Glu
         50                  55                  60

Phe Ser Lys Ala Ile Asp Met Tyr Thr Lys Ala Leu Glu Leu His Pro
 65                  70                  75                  80

Asn Ser Ala Ile Tyr Tyr Ala Asn Arg Ser Leu Ala His Leu Arg Gln
             85                  90                  95

Glu Ser Phe Gly Phe Ala Leu Gln Asp Gly Val Ser Ala Val Lys Ala
            100                 105                 110

Asp Pro Ala Tyr Leu Lys Gly Tyr Tyr Arg Arg Ala Ala His Met
            115                 120                 125

Ser Leu Gly Lys Phe Lys Gln Ala Leu Cys Asp Phe Glu Phe Val Ala
            130                 135                 140

Lys Cys Arg Pro Asn Asp Lys Asp Ala Lys Ile Lys Phe Thr Glu Cys
145                 150                 155                 160

Asn Lys Thr Val Lys Met Arg Ala Phe Glu Arg Ala Ile Ala Val Asp
                165                 170                 175

Lys Pro Glu Lys Thr Leu Ser Glu Met Tyr Ser Asp Met Glu Asn Ile
            180                 185                 190

Thr Ile Glu Asp Asp Tyr Lys Gly Pro Gln Leu Glu Asp Gly Lys Val
            195                 200                 205

Thr Leu Lys Phe Met Lys Glu Leu Met Glu His Thr Lys Ala Gln Lys
210                 215                 220

Arg Leu His Arg Lys Phe Ala Tyr Lys Ile Leu Cys Glu Ile Asp Thr
225                 230                 235                 240

Tyr Met Arg Ala Gln Pro Ser Leu Val Asp Ile Thr Val Pro Asp Glu
                245                 250                 255

Glu Lys Glu Thr Ile Cys Gly Asp Ile His Gly Gln Phe Tyr Asp Leu
            260                 265                 270

Met Asn Ile Phe Glu Ile Asn Gly Leu Pro Ser Glu Lys Asn Pro Tyr
        275                 280                 285

Leu Phe Asn Gly Asp Phe Val Asp Arg Gly Ser Phe Ser Val Glu Cys
        290                 295                 300

Ile Glu Thr Leu Phe Gly Phe Lys Leu Leu Tyr Pro Asn His Phe Phe
305                 310                 315                 320

Leu Ala Arg Gly Asn His Glu Ser Ile Asn Met Asn Gln Met Tyr Gly
                325                 330                 335

Glu Thr Gly Glu Val Thr Ala Lys Tyr Thr Ser Ala Met Ala Asp Ile
            340                 345                 350

Phe Thr Gln Val Glu Asn Trp Leu Pro Leu Cys His Cys Ile Asn Gln
            355                 360                 365

Lys Ile Leu Val Met His Gly Gly Leu Phe Ser Thr Glu Asp Val Thr
        370                 375                 380

Leu Asp His Ile Arg Arg Ile Glu Arg Asn Cys Gln Pro Pro Glu Glu
385                 390                 395                 400

Gly Leu Met Cys Glu Leu Leu Trp Ser Asp Pro Gln Gln Trp Met Gly
                405                 410                 415

Leu Gly Gln Ser Lys Arg Gly Val Gly Ile Gln Phe Gly Pro Asp Val
            420                 425                 430
```

```
Thr Glu Lys Glu Cys Lys Asp Asn Asn Leu Asp Tyr Ile Ile Arg Ser
        435                 440                 445

His Glu Val Lys Asp Met Gly Tyr Glu Val Ala His Asn Gly Lys Cys
    450                 455                 460

Ile Thr Val Phe Ser Ala Pro Asn Tyr Cys Asp Thr Met Gly Asn Met
465                 470                 475                 480

Gly Ala Phe Ile Thr Ile Thr Gly Asn Asn Leu Lys Pro Asn Tyr Lys
                485                 490                 495

Ser Phe Glu Ala Val Pro His Pro Asp Val Lys Pro Met Ala Tyr Ala
            500                 505                 510

Asn Ser Leu Met Asn Trp Leu Ala
        515                 520

<210> SEQ ID NO 22
<211> LENGTH: 524
<212> TYPE: PRT
<213> ORGANISM: Caenorhabditis elegans
<220> FEATURE:
<221> NAME/KEY: PEPTIDE
<222> LOCATION: (1)
<223> OTHER INFORMATION: PP5

<400> SEQUENCE: 22

Met Ala Ala Thr Ile Thr Asp Asp Ile Val Ala Thr Val Leu Glu Ser
 1               5                  10                  15

Ile Glu Glu Lys Ser Tyr Glu Asp Lys Glu Lys Ala Gly Met Ile
            20                  25                  30

Lys Asp Glu Ala Asn Gln Phe Phe Lys Asp Gln Val Tyr Asp Val Ala
        35                  40                  45

Ala Asp Leu Tyr Ser Val Ala Ile Glu Ile His Pro Thr Ala Val Leu
    50                  55                  60

Tyr Gly Asn Arg Ala Gln Ala Tyr Leu Lys Lys Glu Leu Tyr Gly Ser
65                  70                  75                  80

Ala Leu Asp Asp Ala Asp Asn Ala Ile Ala Ile Asp Pro Ser Tyr Val
                85                  90                  95

Lys Gly Phe Tyr Arg Arg Ala Thr Ala Asn Met Ala Leu Gly Arg Phe
            100                 105                 110

Lys Lys Ala Leu Thr Asp Tyr Gln Ala Val Val Lys Val Cys Pro Asn
        115                 120                 125

Asp Lys Asp Ala Arg Ala Lys Phe Asp Glu Cys Ser Lys Ile Val Arg
    130                 135                 140

Arg Gln Lys Phe Glu Ala Ala Ile Ser Thr Asp His Asp Lys Lys Thr
145                 150                 155                 160

Val Ala Glu Thr Leu Asp Ile Asn Met Ala Ile Glu Asp Ser Tyr Asp
                165                 170                 175

Gly Pro Arg Leu Glu Asp Lys Ile Thr Lys Glu Phe Val Leu Gln Leu
            180                 185                 190

Ile Lys Thr Phe Lys Asn Gln Gln Lys Leu His Lys Lys Tyr Ala Phe
        195                 200                 205

Lys Met Leu Leu Glu Phe Tyr Asn Tyr Val Lys Ser Leu Pro Thr Met
    210                 215                 220

Val Glu Ile Thr Val Pro Thr Gly Lys Lys Phe Thr Ile Cys Gly Asp
225                 230                 235                 240

Val His Gly Gln Phe Tyr Asp Leu Cys Asn Ile Phe Glu Ile Asn Gly
                245                 250                 255

Tyr Pro Ser Glu Thr Asn Pro Tyr Leu Phe Asn Gly Asp Phe Val Asp
```

-continued

```
                    260                 265                 270
Arg Gly Ser Phe Ser Val Glu Thr Ile Phe Thr Met Ile Gly Phe Lys
            275                 280                 285
Leu Leu Pro Asn His Phe Phe Met Ser Arg Gly Asn His Glu Ser Asp
        290                 295                 300
Val Met Asn Lys Met Tyr Gly Phe Glu Gly Glu Val Lys Ala Lys Tyr
305                 310                 315                 320
Thr Gln Gln Met Cys Asp Met Phe Thr Glu Thr Phe Cys Trp Leu Pro
                325                 330                 335
Leu Cys His Leu Ile Asn Glu Lys Ile Phe Val Cys His Gly Gly Leu
            340                 345                 350
Phe Lys Glu Asp Gly Val Thr Leu Glu Asp Ile Arg Lys Thr Asp Arg
        355                 360                 365
Asn Arg Gln Pro Pro Asp Glu Gly Ile Met Cys Asp Leu Leu Trp Glu
    370                 375                 380
Lys Asn Trp Lys Asn Leu Lys Ile Leu Tyr Pro Asp Gly Lys Ile Asn
385                 390                 395                 400
Lys Asn Ser Asn Cys Gln Pro Lys Thr Cys Lys Asn Ala Ser Asp Pro
                405                 410                 415
Gln Pro Ile Asn Gly Arg Ser Pro Ser Lys Arg Gly Val Gly Cys Gln
            420                 425                 430
Phe Gly Pro Asp Val Thr Ser Lys Trp Cys Glu Thr Asn Gly Ile Glu
        435                 440                 445
Tyr Val Val Arg Ser His Glu Val Lys Pro Gly Tyr Glu Met His
    450                 455                 460
His Asn Gly Gln Cys Phe Thr Val Phe Ser Ala Pro Asn Tyr Cys Asp
465                 470                 475                 480
Gln Met Asn Asn Lys Gly Ala Phe Ile Thr Ile Thr Gly Asp Asn Leu
                485                 490                 495
Thr Pro Arg Phe Thr Pro Phe Asp Ala Val Pro His Pro Lys Leu Pro
            500                 505                 510
Pro Met Ala Tyr Ala Asn Ser Leu Phe Gly Phe Asn
        515                 520
```

<210> SEQ ID NO 23
<211> LENGTH: 6
<212> TYPE: PRT
<213> ORGANISM: Artificial Sequence
<220> FEATURE:
<223> OTHER INFORMATION: PP2A motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 23

```
Gly Asp Xaa His Gly Gln
  1               5
```

<210> SEQ ID NO 24
<211> LENGTH: 7
<212> TYPE: PRT
<213> ORGANISM: Artificial Sequence
<220> FEATURE:
<223> OTHER INFORMATION: PP2A motif
<220> FEATURE:
<221> NAME/KEY: misc_feature
<222> LOCATION: (3)..(3)
<223> OTHER INFORMATION: Xaa can be any naturally occurring amino acid
<220> FEATURE:

```
-continued

<221> NAME/KEY: misc_feature
<222> LOCATION: (5)..(5)
<223> OTHER INFORMATION: Xaa can be any naturally occurring amino acid

<400> SEQUENCE: 24

Gly Asp Xaa Val Xaa Arg Gly
  1               5

<210> SEQ ID NO 25
<211> LENGTH: 5
<212> TYPE: PRT
<213> ORGANISM: Artificial Sequence
<220> FEATURE:
<223> OTHER INFORMATION: PP2A motif

<400> SEQUENCE: 25

Arg Gly Asn His Glu
  1               5

<210> SEQ ID NO 26
<211> LENGTH: 6
<212> TYPE: PRT
<213> ORGANISM: Artificial Sequence
<220> FEATURE:
<223> OTHER INFORMATION: C-termial consensus sequence

<400> SEQUENCE: 26

Ser Ala Pro Asn Tyr Cys
  1               5
```